United States Patent
Payton

(10) Patent No.: US 10,736,324 B2
(45) Date of Patent: Aug. 11, 2020

(54) INORGANIC PARTICULATE CONTAINING ANTIMICROBIAL METAL

(71) Applicant: ImerTech SAS, Paris (FR)

(72) Inventor: Desmond Charles Payton, St. Austell (GB)

(73) Assignee: ImerTech SAS, Paris (FR)

( * ) Notice: Subject to any disclaimer, the term of this patent is extended or adjusted under 35 U.S.C. 154(b) by 109 days.

(21) Appl. No.: 15/736,341

(22) PCT Filed: Aug. 12, 2016

(86) PCT No.: PCT/GB2016/052515
§ 371 (c)(1),
(2) Date: Dec. 14, 2017

(87) PCT Pub. No.: WO2017/029482
PCT Pub. Date: Feb. 23, 2017

(65) Prior Publication Data
US 2018/0168164 A1 Jun. 21, 2018

(30) Foreign Application Priority Data

Aug. 14, 2015 (GB) .................................. 1514490.0
Jun. 30, 2016 (GB) .................................. 1611468.8

(51) Int. Cl.
| | | |
|---|---|---|
| *A01N 59/16* | (2006.01) | |
| *C02F 1/50* | (2006.01) | |
| *A01N 25/08* | (2006.01) | |
| *A61L 2/238* | (2006.01) | |

(52) U.S. Cl.
CPC ............. *A01N 59/16* (2013.01); *A01N 25/08* (2013.01); *C02F 1/505* (2013.01); *A61L 2/238* (2013.01)

(58) Field of Classification Search
CPC ..... A61K 47/6923; A01N 59/16; A01N 25/08
See application file for complete search history.

(56) References Cited

U.S. PATENT DOCUMENTS

| | | |
|---|---|---|
| 5,159,682 A | 10/1992 | Toyonaga et al. |
| 5,180,585 A | 1/1993 | Jacobson et al. |
| 5,714,430 A | 2/1998 | Gehrer et al. |
| 8,205,613 B2 | 6/2012 | Kladders |
| 2006/0216322 A1 | 9/2006 | Tsuchibe et al. |
| 2010/0260866 A1 | 10/2010 | Lu |
| 2012/0301720 A1 | 11/2012 | Koban et al. |

FOREIGN PATENT DOCUMENTS

| | | |
|---|---|---|
| CA | 2309348 | 9/1991 |
| CN | 101 480 194 A | 7/2009 |
| CN | 101480194 A | 7/2009 |
| DE | 44 25 278 A1 | 1/1996 |
| EP | 0 251 783 A2 | 1/1988 |
| EP | 2 480 499 A | 8/2012 |
| GB | 777 679 A | 6/1957 |
| JP | A-H02-268104 | 11/1990 |
| JP | A-H05-112415 | 5/1993 |
| JP | H07 17803 A | 1/1995 |
| JP | A-H08-337507 | 12/1996 |
| JP | H11 236304 A | 8/1999 |
| JP | 2000-256102 A | 9/2000 |
| WO | WO 2006/084411 A1 | 8/2006 |
| WO | WO 2010/017049 A2 | 2/2010 |
| WO | WO 2010/071831 A2 | 6/2010 |
| WO | WO 2011/037523 A1 | 3/2011 |
| WO | WO 2012/161603 A2 | 11/2012 |
| WO | WO 2013/007289 A1 | 1/2013 |
| WO | WO 2016/062233 A1 | 4/2016 |
| WO | WO 2016/108044 A2 | 7/2016 |

OTHER PUBLICATIONS

Sarioglu ("Removal of ammonium from municipal wastewater using natural Turkish (Dogantepe) zeolite" Separation and Purification Technology 41 (2005) 1-11).*
JP0717803 machine translation, underlying document published 1995.*
International Search Report and Written Opinion dated Sep. 26, 2016, in International Application No. PCT/GB2016/052515 (14 pgs.).
Fondevila, M., "Potential use of silver nanoparticles as an additive in animal feeding", In: "Silver nanoparticles", Mar. 1, 2010, pp. 325-334.

\* cited by examiner

*Primary Examiner* — Kortney L. Klinkel
(74) *Attorney, Agent, or Firm* — Finnegan, Henderson, Farabow, Garrett & Dunner, LLP

(57) ABSTRACT

Compositions comprising an inorganic particulate mineral and an antimicrobial metal, methods of making said compositions, use of said compositions in a coating composition or in a polymeric article, use of said compositions to inhibit the growth of one or more microbes and use of said compositions to eliminate one or more microbes, for example from a liquid.

17 Claims, No Drawings

INORGANIC PARTICULATE CONTAINING ANTIMICROBIAL METAL

CLAIM FOR PRIORITY

This application is a U.S. national phase entry under 35 U.S.C. § 371 from PCT International Application No. PCT/GB2016/052515, filed Aug. 12, 2016, which claims the benefit of priority of GB Application Nos. 1514490.0, filed Aug. 14, 2015, and 1611468.8, filed Jun. 30, 2016, to each of which this application claims priority and each of which is incorporated herein by reference.

TECHNICAL FIELD

The present invention relates generally to compositions comprising an inorganic particulate mineral and an antimicrobial metal. In particular embodiments, the present invention relates to compositions comprising calcium carbonate and an antimicrobial metal such as silver. The present invention further relates to the use of these compositions to eliminate one or more microbes or to inhibit the growth of one or more microbes. For example, the present invention relates to the use of these compositions in polymeric articles, in coating compositions, in surface-mineralized substrates, in purifying systems and in animal feed. The present invention also relates to methods of preparing said compositions comprising an inorganic particulate mineral and an antimicrobial metal.

BACKGROUND

Inorganic particulate minerals are used in a wide variety of applications. For example, inorganic particulate minerals may be used as a filler or extender in numerous materials such as adhesives, sealants, glass, ceramics, films, rubber, paints, papers and plastics. The inorganic particulate mineral may provide advantageous properties such as colour, opacity, gloss, rheology, hardness, chemical resistance, thermal resistance and thermal conductivity. The inorganic particulate mineral may also be used to reduce the amount of another component in a composition, for example, to reduce the toxicity and/or cost of the composition.

Inorganic particulate minerals are often stored, sold and transported as dry mineral or in aqueous suspensions. The inorganic particulate mineral is often kept for days or weeks before it is used in its intended application. The inorganic particulate mineral may be combined with various additives that assist in providing or maintaining favourable properties. The additives may also assist in imparting these favourable properties on the materials and products into which the inorganic particulate mineral is incorporated.

The inorganic particulate mineral may be subject to contamination by microbes such as bacteria, which over a period of time multiply. This can negatively affect the properties of the inorganic particulate mineral, for example by causing discolouration or malodour. It may also result in the contamination of further materials and products into which the inorganic particulate mineral is incorporated. It is thus desirable to reduce the number of microbes (e.g. eliminate) in compositions comprising inorganic particulate mineral and/or to prevent of limit the growth of microbes in these compositions.

SUMMARY

In a first aspect of the present invention, there is provided a composition comprising an inorganic particulate mineral and an antimicrobial metal.

In certain embodiments, the antimicrobial metal is incorporated within the particles of the inorganic particulate mineral. Thus, in a further aspect of the present invention there is provided a composition comprising an inorganic particulate mineral and an antimicrobial metal, wherein the antimicrobial metal is incorporated within the particles of the inorganic particulate mineral.

In certain embodiments, the inorganic particulate mineral is calcium carbonate that does not comprise pores. Thus, in a further aspect of the present invention there is provided a composition comprising calcium carbonate and an antimicrobial metal, wherein the calcium carbonate does not comprise pores. In certain embodiments, the calcium carbonate does not comprise pores in which the antimicrobial metal may be deposited. In certain embodiments, the calcium carbonate is not coral sand and/or is not derived from coral sand. Thus, in a further aspect of the present invention there is provided a composition comprising a calcium carbonate that is not coral sand and/or is not derived from coral sand and an antimicrobial metal.

In certain embodiments, the inorganic particulate mineral is precipitated calcium carbonate (PCC). Thus, in a further aspect of the present invention there is provided a composition comprising PCC and an antimicrobial metal.

In certain embodiments, the antimicrobial metal is provided in the composition in the form of particles of an antimicrobial metal compound. Thus, in a further aspect of the present invention there is provided a composition comprising particles of an inorganic particulate mineral and particles of an antimicrobial metal compound.

In certain embodiments, the composition is an aqueous suspension and the antimicrobial metal is in solution. Thus, in a further aspect of the present invention there is provided an aqueous suspension comprising an inorganic particulate mineral and an antimicrobial metal, wherein the antimicrobial metal is in solution. In certain embodiments, the antimicrobial metal is an antimicrobial metal ion. In certain embodiments, some of the antimicrobial metal may be adsorbed on the surface of the inorganic particulate mineral. In certain embodiments, some of the antimicrobial metal may form an antimicrobial metal compound, which may be adsorbed on the surface of the inorganic particulate mineral.

In certain embodiments, the antimicrobial metal (e.g. antimicrobial metal compound) is present (e.g. adsorbed) on the surface of the inorganic particulate mineral. Thus, in a further aspect of the present invention there is provided a composition comprising an inorganic particulate mineral and an antimicrobial metal (e.g. antimicrobial metal compound), wherein the antimicrobial metal (e.g. antimicrobial metal compound) is present (e.g. adsorbed) on the surface of the inorganic particulate mineral. When the composition is an aqueous suspension, some of the antimicrobial metal may, for example, be in solution, for example as an antimicrobial metal ion.

In certain embodiments, the antimicrobial metal is incorporated within the particles of the inorganic particulate mineral and the particles of inorganic particulate mineral do not include silver nanoparticles embedded in their structure. Thus, in a further aspect of the present invention there is provided a composition comprising an inorganic particulate mineral and an antimicrobial metal, wherein the antimicrobial metal is incorporated within the particles of the inorganic particulate mineral and the particles of inorganic particulate mineral do not include silver nanoparticles embedded in their structure.

In certain embodiments, the antimicrobial metal is incorporated within the particles of the inorganic particulate mineral and the size of the particles of antimicrobial metal within the particles of the inorganic particulate mineral is greater than 50 nm. Thus, in a further aspect of the present invention there is provided a composition comprising an inorganic particulate mineral and an antimicrobial metal, wherein the antimicrobial metal is incorporated within the particles of the inorganic particulate mineral and the size of the particles of antimicrobial metal within the particles of the inorganic particulate mineral is greater than 50 nm.

In a further aspect of the present invention there is provided a method of making a composition or aqueous suspension of any aspect of the present invention. The method comprises combining the inorganic particulate mineral and the antimicrobial metal. Where the composition is an aqueous suspension, the method comprises combining the inorganic particulate mineral, the antimicrobial metal and water. In certain embodiments, the method comprises combining the inorganic particulate mineral and the antimicrobial metal to incorporate the antimicrobial metal within the particles of the inorganic particulate mineral.

In a further aspect of the present invention there is provided a method of making a composition of any aspect of the present invention comprising preparing a synthetic inorganic particulate mineral in the presence of the antimicrobial metal. In certain embodiments, the method comprises preparing precipitated calcium carbonate (PCC) in the presence of the antimicrobial metal.

In a further aspect of the present invention there is provided a method of making a composition comprising an inorganic particulate mineral and an antimicrobial metal comprising combining an inorganic particulate mineral and an antimicrobial metal compound. In certain embodiments, the method comprises combining particles of an inorganic particulate mineral and particles of an antimicrobial metal compound.

In a further aspect of the present invention there is provided a use of a composition or aqueous suspension of any aspect of the present invention to eliminate or reduce the number of one or more microbes. In certain embodiments, the composition may be used to eliminate or reduce the number of one or more microbes from a composition comprising inorganic particulate mineral.

In a further aspect of the present invention there is provided a use of a composition or aqueous suspension of any aspect of the present invention to inhibit the growth of one or more microbes. In certain embodiments, the composition may be used to inhibit the growth of one or more microbes in a composition comprising inorganic particulate mineral.

In a further aspect of the present invention there is provided a use of a composition or aqueous suspension of any aspect of the present invention in a coating composition, wherein the coating composition comprises a polymeric binder. In certain embodiments, the composition or aqueous suspension is used to eliminate or reduce the number or inhibit the growth of one or more microbes in the coating composition.

In a further aspect of the present invention there is provided a coating composition comprising a polymeric binder and a composition or aqueous suspension of any aspect of the present invention.

In a further aspect of the present invention there is provided a use of a composition or aqueous suspension of any aspect of the present invention as a polymer additive. In certain embodiments, the composition or aqueous suspension is used to eliminate or reduce the number or inhibit the growth of one or more microbes in the polymer.

In a further aspect of the present invention there is provided a polymeric article comprising a polymer and a composition or aqueous suspension of any aspect of the present invention.

In a further aspect of the present invention there is provided a use of a composition or aqueous suspension of any aspect of the present invention in a purification system. In a further aspect there is provided a use of a composition or aqueous suspension of any aspect of the present invention to substantially remove, for example to remove, one or more microbes from a liquid.

In a further aspect of the present invention there is provided a use of a composition or aqueous suspension of any aspect of the present invention in animal feed, for example in chicken feed. In a further aspect there is provided a use of a composition or aqueous suspension of any aspect of the present invention in animal feed to eliminate or reduce the number or inhibit the growth of one or more microbes in an animal product.

In a further aspect of the present invention there is provided an animal feed composition comprising a composition or aqueous suspension of any aspect of the present invention.

In a further aspect of the present invention there is provided a use of a composition or aqueous suspension of any aspect of the present invention in a surface-mineralized substrate. In certain embodiments the composition or aqueous suspension of any aspect of the invention is embedded into a surface region of the substrate and/or is attached to a surface of the substrate.

In a further aspect of the present invention there is provided a surface-mineralized substrate, the substrate comprising a composition or aqueous suspension of any aspect of the present invention embedded into a surface region thereof and/or attached to a surface thereof.

In certain embodiments of any aspect of the present invention the inorganic particulate mineral does not comprise pores. In certain embodiments, the inorganic particulate mineral does not comprise pores in which the antimicrobial metal (e.g. antimicrobial metal compound) is or may be deposited.

In certain embodiments of any aspect of the present invention, the inorganic particulate mineral is selected from the group consisting of alkali earth metal carbonate, talc, mica, zeolite and combinations thereof. In certain embodiments, the inorganic particulate mineral is an alkali earth metal carbonate. In certain embodiments, the inorganic particulate mineral is calcium carbonate. In certain embodiments, the inorganic particulate mineral is precipitated calcium carbonate (PCC). In certain embodiments, the inorganic particulate mineral is a synthetic inorganic particulate mineral. In certain embodiments, the inorganic particulate mineral is synthetic calcium carbonate (e.g. PCC), synthetic talc, synthetic mica or synthetic zeolite. In certain embodiments, the inorganic particulate mineral is an alkali earth metal carbonate that is not coral sand and is not derived from coral sand. In certain embodiments, the inorganic particulate mineral is calcite. In certain embodiments, the inorganic particulate mineral is synthetic calcite (e.g. precipitated calcite). In certain embodiments, the inorganic particulate mineral is not vaterite. In certain embodiments, the inorganic particulate mineral is kaolin.

In certain embodiments of any aspect of the present invention, the inorganic particulate mineral has a steepness factor of at least about 10. In certain embodiments, the inorganic particulate mineral has a steepness factor of at least about 20. In certain embodiments, the inorganic particulate mineral has a steepness factor ranging from about 10 to about 90.

In certain embodiments of any aspect of the present invention, at least about 90% of particles of the inorganic particulate mineral are smaller than 5 microns. In certain embodiments, at least about 50% of particles of the inorganic particulate mineral are smaller than 2 microns.

In certain embodiments of any aspect of the present invention the composition is an aqueous slurry. In certain embodiments, the aqueous slurry has a solids content of at least about 50 wt %. In certain embodiments, the aqueous slurry has a solids content of at least about 60 wt %. In certain embodiments, the aqueous slurry has a Brookfield viscosity equal to or less than about 1200 mPa·s.

In certain embodiments of any aspect of the present invention, the antimicrobial metal is selected from the group consisting of silver, cobalt, nickel, copper, iron, mercury, lead, zinc, zirconium, molybdenum, bismuth, gold, aluminium, magnesium, niobium, silicon, tantalum, hafnium, lanthanum, tungsten, calcium, titanium, vanadium, cerium, strontium, tin, lithium and combinations thereof. In certain embodiments, the antimicrobial metal is silver.

In certain embodiments of any aspect of the present invention, the antimicrobial metal is present in the composition in an amount ranging from about 0.1% to about 10% by weight of the inorganic particulate mineral. In certain embodiments, the antimicrobial metal is present in the composition in an amount ranging from about 0.2% to about 5% by weight of the inorganic particulate mineral.

In certain embodiments of any aspect of the present invention, the antimicrobial metal is incorporated within the particles of the inorganic particulate mineral. In certain embodiments, the antimicrobial metal is chemically bonded to the inorganic particulate mineral, for example to form an antimicrobial metal compound. In certain embodiments, the inorganic particulate mineral is an alkali metal earth carbonate and the antimicrobial metal is an antimicrobial metal carbonate. In certain embodiments, the inorganic particulate mineral is one or more of talc, mica and zeolite and the antimicrobial metal is an antimicrobial metal silicate. In certain embodiments, the antimicrobial metal (e.g. antimicrobial metal compound) is physically bonded to the inorganic particulate mineral, by one or more of Van der Waals forces, London dispersion forces, dipole-dipole interactions, hydrogen bonding and Debye forces.

In certain embodiments, the antimicrobial metal (e.g. antimicrobial metal compound) is distributed, for example evenly distributed, throughout the particles of the inorganic particulate mineral. In certain embodiments, the antimicrobial metal (e.g. antimicrobial metal compound) is positioned at the core of the particles of the inorganic particulate mineral.

In certain embodiments, particles of the antimicrobial metal compound are chemically or physically bonded to particles of the inorganic particulate mineral, for example by one or more of Van der Waals forces, London dispersion forces, dipole-dipole interactions, hydrogen bonding and Debye forces.

In certain embodiments of any aspect of the present invention, the composition or aqueous suspension has a toxic effect on one or more microbes.

In certain embodiments of any aspect of the present invention, the composition is substantially devoid or is devoid of biocide.

In certain embodiments of any aspect of the present invention, the composition is substantially devoid or is devoid of microbes.

In certain embodiments of any aspect of the present invention, the antimicrobial metal is or is provided as a metal salt. In certain embodiments, the antimicrobial metal is or is provided as a metal halide or a metal nitrate.

In certain embodiments of any aspect of the present invention, the inorganic particulate mineral is synthetic and the antimicrobial metal is combined with the inorganic particulate mineral during preparation of the synthetic inorganic particulate mineral.

In certain embodiments of any aspect of the present invention, the inorganic particulate mineral is synthetic and the antimicrobial metal compound is formed during preparation of the synthetic inorganic particulate mineral.

In certain embodiments of any aspect of the present invention, the composition or aqueous suspension is used for purification of a liquid or gas, for example to eliminate or reduce the number or inhibit the growth of one or more microbes in a liquid or gas. In certain embodiments, the liquid is water. In certain embodiments, the gas is air. In certain embodiments, the composition or aqueous suspension is used to make the water or air suitable for animal (e.g. human) consumption.

The details, examples and preferences provided in relation to any particular one or more of the stated aspects of the present invention apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION

Inorganic Particulate Mineral Compositions

There is provided herein compositions comprising an inorganic particulate mineral and an antimicrobial metal. The embodiments described herein and all combinations thereof are equally applicable to all aspects of the present invention.

The presence of the antimicrobial metal in these compositions may, for example, have a toxic effect on any microbes present in the composition. For example, the antimicrobial metal may reduce the number of microbes in a composition comprising inorganic particulate mineral, for example over a period of 1 day or 2 days or 3 days or 4 days or 5 days or 6 days or 7 days or 14 days or 21 days or 28 days. For example, the antimicrobial metal may substantially eliminate (e.g. completely eliminate) microbes from a composition comprising an inorganic particulate mineral. For example, the antimicrobial metal may substantially eliminate (e.g. completely eliminate) microbes from a composition comprising an inorganic particulate mineral over a period of 1 day or 2 days or 3 days or 4 days or 5 days or 6 days or 7 days or 14 days or 21 days or 28 days. Alternatively or additionally, the antimicrobial metal may prevent the growth/multiplication of one or more microbes in the composition or may reduce the rate of growth/multiplication (i.e. inhibit the growth/multiplication) of one or more microbes in the composition, for example over a period of 1 day or 2 days or 3 days or 4 days or 5 days or 6 days or 7 days or 14 days or 21 days or 28 days. The presence of the antimicrobial metal in the composition may, for example, have a toxic effect on any microbes present in or on the products in which the inorganic particulate mineral composition is incorporated, or may, for example, have a toxic effect on any microbes present in or on a material on which the inorganic particulate mineral composition and/or product comprising the inorganic particulate mineral composition is applied.

This toxic effect of the antimicrobial metal on any microbes present in the composition may, for example, be due to the oligodynamic toxic effect, which is the toxic effect of metal ions on viruses and living cells, even at relatively low concentrations. The high affinity of cellular proteins for the metallic ions results in the death of the cells due to cumulative effects of the ion within the cells. For example, silver may inactivate enzymes by binding with sulfhydryl groups to form silver sulphides and/or the sulfhydryl-binding propensity of silver ions may disrupt cell membranes.

The term microbe includes, for example, prokaryotic and eukaryotic microorganisms, for example, algae, moulds, spores, bacteria, viruses, archaea, protists, fungi, yeast. The antimicrobial metal in these composition may, for example, have a toxic effect on any one or more of these types of microbes. For example, the antimicrobial metal may have a toxic effect on all of these types of microbes. For example, the antimicrobial metal may have a toxic effect on all microbes.

The antimicrobial metal may, for example, have a toxic effect on one or more bacteria. For example, the antimicrobial metal may have a toxic effect on one or more of Staphylococci, Micrococci, *Escherichia, Escherichia coli, Pseudomonas, Pseudomonas aeruginosa, Pseudomonas vesicularis, Stenotrophomonas maltophilia, Klebsiella pneumonia, S. aureus, S. edidermis, Lactobacillus buchneri, PS aeuginosa, Serratia marcescens, Listeria monocytogenes, B subtilis, B cereus, C albicans, C parapsilosis, C bordinii, Sacc cerevisae, Sacc rouxii*, pink yeast, odium sp., *Aspergillus flavus, Aspergillus fumigates, Aspergillus niger, Aspergillus glaugus, Penicillium notatum, Cladosporium herbarum, Trichothecium ciride*, acternaria alternate, *Myrothecium verruccaria, Verticillium psalliotae*, Bacilli, Salmonella, Shigella, pionibacterium, Streptococci, *Cprumebacterium, Treponema, Fusobacterium, Bifidobacterium, Lactobacillus, Actinomyces, Candida, Malazessia, Aspergillus, Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp., *Pseudomonas putida, Pseudomonas mendocina, Pseudomonas fluorescens, Pseudomonas alcaligenes, Pseudomonas pseudoalcaligenes, Pseudomonas entomophila, Pseudomonas syringae, Methylobacterium extorquens, Methylobacterium radiotolerants, Methylobacterium dichloromethanicum, Methylobacterium organophilu*, and *Hyphomicrobium zavarzini*. For example, the antimicrobial metal may have a toxic effect on all of these types of bacteria. For example, the antimicrobial metal may have a toxic effect on all bacteria.

The compositions comprising inorganic particulate mineral may, therefore, be substantially devoid of microbes. The composition may be considered to be "substantially devoid" of microbes if it has a total viable count equal to or less than about 1000 colony forming units (cfu) per millilitre, for example equal to or less than about 800 cfu/ml, for example equal to or less than about 500 cfu/ml, for example equal to or less than about 100 cfu/ml, for example equal to or less than about 10 cfu/ml.

The total viable count of the compositions may range from about 0 cfu/ml to about 1,000,000 cfu/ml. For example, the total viable count of the compositions may range from about 10 cfu/ml to about 1,000,000 cfu/ml, for example from about 100 cfu/ml to about 500,000 cfu/ml, for example from about 100 cfu/ml to about 100,000 cfu/ml. The total viable count of the compositions may range from about 0 cfu/ml to about 10,000 cfu/ml, for example from about 10 cfu/ml to about 10,000 cfu/ml, for example from about 0 cfu/ml to about 1000 cfu/ml, for example from about 10 cfu/ml to about 1000 cfu/ml, for example from about 10 cfu/ml to about 100 cfu/ml.

The microbe level, for example the total viable count, of the compositions may be measured using growth medium such as Petrifilm or dipslides. The material under test (for example the aqueous suspension of inorganic particulate material) is diluted with a buffer solution and a measured amount of the dilution is placed on a growth medium (for example, Petrifilm). This is incubated for 48 hours, after which time the number of colonies (e.g. of bacteria) is counted. Each colony has developed from one single microbe (e.g. bacterium) or colony forming unit (cfu). Therefore, the number of colonies, multiplied by the dilution factor, is equivalent to the number of original colony forming units per gram or millilitre of slurry.

For example, the total viable count of a composition may be measured by:
  if the composition is an aqueous slurry, it is thoroughly mixed by shaking its container vigorously;
  measuring the required weight or volume of the sample. For example, if the results are to be recorded as colony forming units per g (cfu/g), a container containing the buffer solution is placed on the balance and the balance is set to zero. Approximately 1 g of slurry is weighed into the container and its weight is recorded to within 0.1 g. The contents of the container are mixed by shaking it vigorously. If the results are to be recorded as colony forming units per ml (cfu/ml), 1 ml of slurry may be added to a container containing the buffer solution. The contents of the container are mixed by shaking it vigorously;
  distributing the diluted sample evenly on the growth medium. The plate may be left undisturbed for at least one minute to allow the gel to solidify;
  incubating the contents of the growth medium (for example Petrifilm plates) for 48 hours±2 hours at 30° C.±2° C.;
  counting the number of colonies on the growth medium (for example Petrifilm);
  calculating the total viable count of the sample by multiplying the number of colonies on the growth medium (for example Petrifilm) by the dilution factor and dividing this by the weight or volume of the sample which was plated on the growth medium. For example:

$$cfu/\text{ml} = \frac{\text{number of colonies on growth medium} \times \text{dilution factor}}{\text{volume plated on growth medium}}.$$

The total viable count of the composition may be measured immediately after preparation (total viable count at time 0). The total viable count of the composition may be measured 1 day after preparation, 3 days after preparation, 5 days after preparation or 7 days after preparation. The total viable count of the composition may be measured up to 1 week after preparation, up to 2 weeks after preparation, up to 3 weeks after preparation, up to 4 weeks after preparation, up to 5 weeks after preparation or up to 6 weeks after preparation.

The antimicrobial metal may, for example, reduce the rate of (e.g. inhibit) microbe growth in the composition. Alternatively or additionally, the antimicrobial metal may, for example, reduce the total number of (e.g. eliminate) microbes from the composition. For example, after a certain period of time, a composition comprising an inorganic particulate mineral and an antimicrobial metal as described herein may have a microbe content that is less than the microbe content of the same composition without the antimicrobial metal. For example, after a certain period of time, a composition comprising an inorganic particulate mineral and an antimicrobial metal as described herein may have a microbe content that is at least about 20% less than the microbe content of the same composition without the antimicrobial metal. For example, after a certain period of time, a composition comprising an inorganic particulate mineral and an antimicrobial metal as described herein may have a microbe content that is at least about 30% or at least about 40% or at least about 50% or at least about 60% or at least about 70% or at least about 80% or at least about 90% less than the microbe content of the same composition without the antimicrobial metal. For example, after a certain period of time, a composition comprising an inorganic particulate mineral and an antimicrobial metal as described herein may have a microbe content that is up to about 100%, or up to about 98% or up to about 95% or up to about 92% less than the microbe content of the same composition without the antimicrobial metal.

The period of time may, for example, be immediately after preparation, 1 day after preparation, 3 days after preparation, 5 days after preparation or 7 days after preparation. The period of time may, for example, be up to 1 week after preparation, up to 2 weeks after preparation, up to 3 weeks after preparation, up to 4 weeks after preparation, up to 5 weeks after preparation or up to 6 weeks after preparation.

Any product that the composition comprising an inorganic particulate mineral and an antimicrobial metal as described herein is incorporated into or is applied onto may also have a microbe content as specified above in relation to the inorganic particulate mineral composition.

The toxic effect of the antimicrobial metal may, for example, allow the compositions comprising inorganic particulate mineral to be prepared with a reduced amount or without further biocides. This may, for example, be advantageous for regulatory purposes and/or cost purposes.

The biocide(s) may, for example, be an aldehyde-releasing biocide, an aldehyde-based biocide, a phenolic biocide, an isothiazoline biocide, or any mixture thereof. The biocide may be selected from one or more of the following: formaldehyde, hydrogen peroxide, sodium hypochlorite, acetaldehyde, glyoxal, succinaldehyde, glutaraldehyde, 2-propenal, phthalic dialdehyde and mixtures thereof, and in certain embodiments is formaldehyde, glutaraldehyde, benzyl alcoholmono(poly)-hemiformal, ethyleneglycolhemiformal (EGHF), [1,2-Ethanediylbis(oxy)]-bis-methanol, tetrahydro-1, 3, 4, 6-tetrakis(hydroxylmethyl)imidazo [4,5-d] imidazole-2,5 (1H,3H)-dione (also commonly referred to as TetraMethylolAcetyleneDiurea TMAD), orthophenylphenol (OPP), 2-methyl-4-isothiazoline-3-one (MIT), 5-chloro-2-methyl-2H-isothiazolin-3-one (CIT), 1,2-benzisothiazoline-3-one (BIT), or mixtures thereof. The biocide may be a combination of 2-methyl-4-isothiazoline-3-one (MIT) and 1,2-benzisothiazoline-3-one (BIT). The biocide(s) may, for example, be or include aminoalcohols such as ethanolamine and dimethylethanol amine. The biocide(s) may, for example, be or include alkanolamines such as 2-amino-2-methyl-1-propanol (AMP).

The amount of biocide present in the compositions may, for example, range from 0 ppm to about 2000 ppm, for example from about 5 ppm to about 2000 ppm, for example from about 10 ppm to about 2000 ppm, for example from about 50 ppm to about 2000 ppm, for example from about 50 ppm to about 1500 ppm, for example from about 50 ppm to about 1000 ppm. The one or more biocide(s) may be present in the composition in an amount ranging from about 50 ppm to about 800 ppm, or from about 50 ppm to about 650 ppm, or from about 50 ppm to about 500 ppm or from about 50 ppm to about 400 ppm. The compositions may, for example, be considered to be "substantially devoid" of biocide if it comprises equal to or less than about 1000 ppm of biocide, for example equal to or less than about 800 ppm or equal to or less than about 600 ppm or equal to or less than about 500 ppm or equal to or less than about 400 ppm or equal to or less than about 300 ppm or equal to or less than about 200 ppm or equal to or less than about 100 ppm or equal to or less than about 50 ppm or equal to or less than about 10 ppm of biocide. The composition may, for example, be devoid of biocide.

The composition may, for example, be an aqueous suspension. The solids content of the aqueous suspension may, for example, be equal to or greater than about 50% by weight of the composition. For example, the solids content of the composition may be equal to or greater than about 55% or 60% by weight of the composition. For example, the solids content of the composition may range from about 60% to about 85% by weight, for example from about 66% to about 82% by weight, for example from about 70% to about 80% by weight of the composition. For example, the solids content of the composition may be from about 73% to about 79% by weight of the composition, for example the solids content of the composition may be about 76% by weight of the composition. The solids content of the aqueous suspension is the percentage mass of material remaining after the aqueous suspension has been dried to contain zero moisture. Alternatively, the composition may be a dry mineral composition comprising less than about 5 wt % water or less than about 4 wt % water or less than about 3 wt % water or less than about 2 wt % water or less than about 1 wt % water.

The composition may, for example have a viscosity equal to or less than about 1200 mPa·s. For example, the composition may have a viscosity equal to or less than about 1100 mPa·s, for example equal to or less than about 1000 mPa·s, for example equal to or less than about 900 mPa·s, for example equal to or less than about 800 mPa·s, for example equal to or less than about 700 mPa·s, for example equal to or less than about 600 mPa·s, for example equal to or less than about 500 mPa·s. For example, the composition may have a viscosity ranging from about 100 mPa·s to about 1200 mPa·s, for example from about 100 mPa·s to about 1000 mPa·s, for example from about 100 mPa·s to about 800 mPa·s, for example from about 100 to about 600 mPa·s, for example from about 100 to about 500 mPa·s, for example from about 100 to about 400 mPa·s.

Unless otherwise stated, viscosity is measured using a Brookfield R.V. viscometer or other similar instrument including spindles. Approximately 200 ml of sample is measured into a container. The temperature of the sample is adjusted to 22° C. A clean, dry spindle is immersed into the sample at a central position within the container. The speed is set to 10 rpm and the viscometer is switched on. The speed is then increased to 100 rpm and the spindle is allowed to rotate for 60 seconds±2 seconds. The viscometer reading is then noted.

Inorganic Particulate Material

Any inorganic particulate mineral capable of being provided in an aqueous suspension may be used in embodiments of the present invention. Suitable inorganic particulate minerals may be selected from one or more of the following: alkaline earth metal carbonate (for example dolomite, i.e. $CaMg(CO_3)_2$), metal sulphate (for example gypsum), metal silicate (e.g. calcium silicate, for example calcium silicate derived from diatomaceous earth (DE), calcium silicate hydrate, vermiculite), metal oxide (for example zinc oxide, iron oxide, chromia, antimony trioxide or silica), diatomite (DE) (e.g. comprising at least about 90% $SiO_2$), perlite, metal hydroxide (e.g. magnesium hydroxide), wollastonite (e.g. high aspect ratio wollastonite), bauxite, talc (for example, French chalk), mica, zinc oxide (for example, zinc white or Chinese white), titania, titanium dioxide (for example, anatase or rutile), zinc sulphide, calcium carbonate (for example precipitated calcium carbonate (PCC), ground calcium carbonate (GCC), for example obtained from limestone, marble and/or chalk, or surface-modified calcium carbonate), barium sulphate (for example, barite, blanc fixe or process white), calcium sulphate, alumina hydrate (for example, alumina trihydrate, light alumina hydrate, lake white or transparent white), clay (for example kaolin (e.g. airfloat kaolin clay, water-washed kaolin clay, delaminated kaolin clay), calcined kaolin, China clay, bentonite or illite clay (e.g. gumbelite, hydromica, hydromuscovite, muscovite, sericite)), zeolites (e.g. natural and synthetic zeolites), activated carbon, carbon black, amorphous silicas, chlorite, feldspar, graphite, huntite, hydromagnesite, hydrotacite, magnesia, magnesite (magnesium carbonate), magnetite, nepheline syenite, olivine, psuedoboehmites, prophylite, Turkish powder, stone powder, pumice, coral sand, silica (e.g. ground silica, novoculite silica, precipitated silica, fumed silica, fumed amorphous silica), aluminosilicates, mineral powder (e.g. fly ash, bark ash, bottom ash, pet coke ash, silica fume, condensed silica fume, rice hull ash, slag, volcanic ash, volcanic tuffs, natural pozzolans) and combinations thereof. The inorganic particulate mineral may be selected from any one or more of the materials listed. The inorganic particulate mineral may comprise a blend of any combination of the listed materials. The inorganic particulate mineral may, for example, be selected from alkali earth metal carbonates, kaolin, talc, mica, zeolite and combinations thereof. For example, the inorganic particulate mineral may be calcium carbonate. For example, the inorganic particulate mineral may be precipitated calcium carbonate. For example, the inorganic particulate mineral may be kaolin. Hereinafter, embodiments of the present invention may tend to be discussed in terms of calcium carbonate or kaolin. However, the invention should not be construed as being limited to such embodiments.

The inorganic particulate mineral may, for example, be synthetic. The inorganic particulate mineral may, for example, be precipitated calcium carbonate (PCC), synthetic talc, synthetic mica, synthetic zeolite or combinations thereof.

The inorganic particulate mineral may, for example, not be porous. For example, the inorganic particulate mineral may not comprise pores in which the antimicrobial metal is or can be deposited.

For example, the inorganic particulate mineral may have a surface area ranging from about 0.1 to about 50 $m^2/g$. For example, the inorganic particulate mineral may have a surface area ranging from about 0.5 to about 50 $m^2/g$ or from about 1 to about 50 $m^2/g$. For example, the inorganic particulate mineral may have a surface area ranging from about 2 to about 45 $m^2/g$, for example from about 5 to about 40 $m^2/g$. The TRISTAR manufactured by Micromeritics is used to determine the specific surface area of a powder or granulated substance by the Brunauer Emmett and Teller (B.E.T.) method. The specific surface area is determined by measuring the quantity of nitrogen gas that is adsorbed as a monomolecular layer on the test sample. The adsorption is carried out at temperatures close to the boiling point of the adsorbate. This is achieved by immersing the test sample in a Dewar flask containing liquid nitrogen. Under these specific conditions the area covered by a molecule of gas is accurately known. Thus, the area of the test material may be determined by measuring the number of molecules adsorbed.

The inorganic particulate mineral may, for example, not be coral sand or derived from coral sand.

When the inorganic particulate mineral used in embodiments of the present invention is obtained from naturally occurring sources, it may be that some mineral impurities will inevitably contaminate the ground material. For example, naturally occurring calcium carbonate occurs in association with other minerals. In general, however, the inorganic particulate mineral used in embodiments of the present invention will contain less than 5% by weight, preferably less than 1% by weight of other mineral impurities.

Calcium carbonate is particularly suitable for use in connection with embodiments of the present invention. Examples of calcium carbonate include ground calcium carbonate (GCC), precipitated calcium carbonate (PCC), dolomite and surface-modified calcium carbonate. The calcium carbonate may, for example, be calcite.

The calcium carbonate may, for example, be synthetic calcite or precipitated calcite. The calcium carbonate may, for example, not be vaterite.

The particulate calcium carbonate used in embodiments of the present invention may be obtained from a natural source by grinding or may be prepared synthetically by precipitation (PCC), or may be a combination of the two, i.e. a mixture of the naturally derived ground material and the synthetic precipitated material. The PCC may also be ground.

Ground calcium carbonate (GCC) is typically obtained by grinding a mineral source such as chalk, marble or limestone, which may be followed by a particle size classification step, in order to obtain a product having the desired degree of fineness. The particulate solid material may be ground autogenously, i.e. by attrition between the particles of the solid material themselves, or alternatively, in the presence of a particulate grinding medium comprising particles of a different material from the calcium carbonate to be ground.

Wet grinding of calcium carbonate involves the formation of an aqueous suspension of the calcium carbonate which may then be ground, optionally in the presence of a suitable dispersing agent. Reference may be made to, for example, EP-A-614948 (the contents of which are incorporated by reference in their entirety) for more information regarding the wet grinding of calcium carbonate.

PCC may be used as the source of particulate calcium carbonate in embodiments of the present invention, and may be produced by any of the known methods available in the art. TAPPI Monograph Series No 30, "Paper Coating Pigments", pages 34-35, the contents of which are incorporated herein by reference, describes the three main commercial processes for preparing precipitated calcium carbonate which is suitable for use in preparing products for use in the paper industry, but may also be used in connection with the embodiments of the present invention. In all three processes, limestone is first calcined to produce quicklime, and the quicklime is then slaked in water to yield calcium hydroxide or milk of lime. In the first process, the milk of lime is directly carbonated with carbon dioxide gas. This process has the advantage that no by-product is formed, and it is relatively easy to control the properties and purity of the calcium carbonate product. In the second process, the milk of lime is contacted with soda ash to produce, by double decomposition, a precipitate of calcium carbonate and a solution of sodium hydroxide. The sodium hydroxide should be substantially completely separated from the calcium carbonate if this process is to be commercially attractive. In the third main commercial process, the milk of lime is first contacted with ammonium chloride to give a calcium chloride solution and ammonia gas. The calcium chloride solution is then contacted with soda ash to produce, by double decomposition, precipitated calcium carbonate and a solution of sodium chloride.

Alternatively, PCC may be made by reacting gypsum (calcium sulphate) with ammonium carbonate or ammonium bicarbonate.

Alternatively, PCC may be made by reacting calcium chloride with sodium carbonate or ammonium carbonate.

The process for making PCC results in very pure calcium carbonate crystals and water. The crystals can be produced in a variety of different shapes and sizes, depending on the specific reaction process that is used. The three main forms of PCC crystals are aragonite, rhombohedral and scalenohedral, all of which are suitable for use in embodiments of the present invention, including mixtures thereof. The calcium carbonate, for example GCC or PCC, may optionally be surface-modified. The calcium carbonate may be coated. The coating may consist of, consist essentially of, or comprise a silane or any salt thereof, for example an organic silane. The calcium carbonate may be coated with a fatty acid or salt thereof. For example, the calcium carbonate may be coated with stearate. The level of coating may be about 0.1 to about 10 wt % based on the total weight of the coated particulate mineral additive, for example between about 0.1 and about 3 wt %, for example between about 0.5 or 0.6 or 0.7 or 0.8 and about 2.0 wt % e.g. about 1.5 wt %. The term "coating" used herein is to be understood broadly, and is not limited, for example, to uniform coatings or to coatings which cover the entire surface area of a particle. Particles in which discrete regions of the surface are modified with a coating will be understood as being coated within the terms of certain embodiments of the present invention.

The inorganic particulate mineral may have a particle size distribution such that at least about 90% of particles are smaller than 5 μm. For example, at least about 91% or at least about 92% or at least about 93% or at least about 94% or at least about 95% or at least about 96% or at least about 97% or at least about 98% or at least about 99% of particles of the inorganic particulate mineral may be smaller than 5 μm. For example from about 90% to about 99% or from about 92% to about 98% of particles of the inorganic particulate mineral may be smaller than 5 μm.

The inorganic particulate mineral may have a particle size distribution such that at least about 50% of particles are smaller than 2 μm. For example, at least about 55%, at least about 60%, or at least about 65% of particles may be smaller than 2 μm. The inorganic particulate mineral may, for example, have a particle size distribution such that at least about 70% of particles are smaller than 2 μm. For example, at least about 72% or at least about 75% or at least about 78% or at least about 80% or at least about 82% or at least about 85% or at least about 88% or at least about 90% or at least about 95% of particles of the inorganic particulate mineral may be smaller than 2 μm. For example from about 50% to about 95% or from about 60% to about 95% or from about 70% to about 95% of particles of the inorganic particulate mineral may be smaller than 2 μm.

The inorganic particulate mineral may, for example, have a $d_{50}$ ranging from about 0.2 μm to about 3 μm. For example, the inorganic particulate mineral may have a $d_{50}$ ranging from about 0.2 μm to about 2.5 μm or from about 0.2 μm to about 2 μm or from about 0.2 μm to about 1.5 μm. For example, the inorganic particulate mineral may have a $d_{50}$ ranging from about 0.5 μm to about 3 μm or from about 0.5 μm to about 2.5 μm or from about 0.5 μm to about 2 μm or from about 0.5 μm to about 1.5 μm.

The inorganic particulate mineral may have a steepness factor of at least about 10. For example, the inorganic particulate mineral may have a steepness factor of at least about 20 or at least about 25 or at least about 30 or at least about 35. The inorganic particulate mineral may, for example have a steepness factor ranging from about 10 to about 90. For example, the inorganic particulate mineral may have a steepness factor ranging from about 10 to about 80 or from about 10 to about 70 or from about 10 to about 60 or from about 10 to about 50. For example, the inorganic particulate mineral may have a steepness factor ranging from about 20 to about 90 or from about 20 to about 80 or from about 20 to about 70 or from about 20 to about 60 or from about 20 to about 50 or from about 20 to about 40.

The steepness factor is defined as the ratio of the $d_{30}$ equivalent spherical diameter (at which 30% by weight of the particles are finer) to the $d_{70}$ equivalent spherical diameter (at which 70% by weight of the particles are finer), multiplied by 100.

Unless otherwise stated, particle size properties referred to herein for the inorganic particulate mineral are as measured in a well known manner by sedimentation of the particulate filler or material in a fully dispersed condition in an aqueous medium using a Sedigraph 5100 machine as supplied by Micromeritics Instruments Corporation, Norcross, Ga., USA (telephone: +17706623620; web-site: www.micromeritics.com), referred to herein as a "Micromeritics Sedigraph 5100 unit". Such a machine provides measurements and a plot of the cumulative percentage by weight of particles having a size, referred to in the art as the 'equivalent spherical diameter' (e.s.d), less than given e.s.d values. The mean particle size $d_{50}$ is the value determined in this way of the particle e.s.d at which there are 50% by weight of the particles which have an equivalent spherical diameter less than that $d_{50}$ value. The $d_{98}$, $d_{90}$ and the $d_{10}$ are the values determined in this way of the particle e.s.d. at which there are 98%, 90% and 10% respectively by weight of the particles which have an equivalent spherical diameter less than that $d_{98}$, $d_{90}$ or $d_{10}$ value.

Antimicrobial Metal

The antimicrobial metal may be any metal that has a toxic effect on one or more microbes. Toxic effect may, for example, mean that the antimicrobial metal results in the elimination or reduction of microbes in a composition or may mean that the antimicrobial metal prevents or reduces the rate of growth/multiplication of one or more microbes. This can be determined by measuring the total viable count of a product as described above. The antimicrobial metal may, for example, be selected from the group consisting of silver, cobalt, nickel, copper, iron, mercury, lead, zinc, zirconium, molybdenum, bismuth, gold, aluminium, magnesium, niobium, silicon, tantalum, hafnium, lanthanum, tungsten, calcium, titanium, vanadium, cerium, strontium, tin, lithium and combinations thereof. The antimicrobial metal may, for example, be silver. Hereinafter, the present invention may be discussed in terms of silver. However, the invention should not be construed as being limited as such.

The antimicrobial metal may, for example, be elemental metal, a metal ion, a compound including the metal (e.g. a metal salt or metal oxide) or a combination thereof. Examples of antimicrobial metal compounds include, but are not limited to, halides (e.g. silver halides such as silver chlorides), oxides (e.g. silver oxides), silicates (e.g. silver silicates (e.g., silver metasilicate ($Ag_2SiO_3$) and silver orthosilicate ($Ag_4SiO_4$)), salts (e.g. silver salts such as silver halogenide, silver nitrate, silver sulfate, silver carboxylates (e.g., silver acetate, silver benzoate, silver carbonate, silver citrate, silver lactate, and silver salicylate)), Hydrogen Peroxide/Antimicrobial metal (e.g. hydrogen peroxide/silver such as Accepta 8102 available from Accepta™ Advanced Chemical Technologies), copper oxides, copper salts (e.g., copper sulfide, copper nitrate, copper carbonate, copper sulfate, copper halogenides, and copper carboxylates), zinc oxides, and zinc salts (e.g., zinc sulfide, zinc silicate, zinc acetate, zinc chloride, zinc nitrate, zinc sulfate, zinc gulconate, zinc lactate, zinc oxalate, zinc iodate, and zinc iodide). In certain embodiments, the antimicrobial metal is one or more of silver, copper, magnesium, aluminum, niobium, silicon, tantalum, zirconium, cobalt, hafnium, lanthanum, tungsten, calcium, titanium, vanadium, cerium, strontium, tin, and zinc.

In certain embodiments, the antimicrobial metal is an antimicrobial metal compound that may be made as a by-product of a process for making the inorganic particulate mineral or may be made by reacting an antimicrobial metal with the inorganic particulate mineral. In certain embodiments, the antimicrobial metal is an antimicrobial metal compound that has an anion that is the same as the anion of the inorganic particulate mineral. For example, where the inorganic particulate mineral is an alkali earth metal carbonate, the antimicrobial metal may be antimicrobial metal carbonate. For example, where the inorganic particulate mineral is talc, mica or zeolite, the antimicrobial metal may be antimicrobial metal silicate.

The antimicrobial metal may, for example, be present in the composition in an amount ranging from about 0.01% to about 10% by weight of the inorganic particulate mineral or from about 0.1% to about 10% by weight of the inorganic particulate mineral. For example, the antimicrobial metal may be present in the composition in an amount ranging from about 0.01% to about 9% or from about 0.1% to about 9% or from about 0.1% to about 8% or from about 0.1% to about 7% or from about 0.1% to about 6% or from about 0.1% to about 5% or from about 0.1% to about 4% or from about 0.1% to about 3% or from about 0.1% to about 2% or from about 0.1% to about 1%, by weight of the inorganic particulate mineral. For example, the antimicrobial metal may be present in the composition in an amount ranging from about 0.2% to about 10% or from about 0.2% to about 9% or from about 0.2% to about 8% or from about 0.2% to about 7% or from about 0.2% to about 6% or from about 0.2% to about 5% or from about 0.2% to about 4% or from about 0.2% to about 3% or from about 0.2% to about 2% or from about 0.2% to about 1%, by weight of the inorganic particulate mineral. For example, the antimicrobial metal may be present in the composition in an amount ranging from about 0.5% to about 10% or from about 0.5% to about 9% or from about 0.5% to about 8% or from about 0.5% to about 7% or from about 0.5% to about 6% or from about 0.5% to about 5% or from about 0.5% to about 4% or from about 0.5% to about 3% or from about 0.5% to about 2% or from about 0.5% to about 1%, by weight of the inorganic particulate mineral. The antimicrobial metal may, for example, be provided in an amount that is toxic to microbes but is not toxic to animals, such as humans. This may, for example, be advantageous in that it allows the composition to be used in particular products, for example in food packaging products, that may be strictly regulated in terms of the type and amount of biocides that can be used. The amount of antimicrobial metal in the composition may, for example, be determined by inductively coupled plasma (ICP) spectroscopy.

The antimicrobial metal may, for example, not be embedded within the structure of the inorganic particulate mineral particles. The antimicrobial metal may, for example, not be silver nanoparticles embedded within the structure of the inorganic particulate mineral particles. The antimicrobial metal may, for example, not be a silver (e.g. elemental silver or a silver salt) colloid.

The antimicrobial metal may, for example, be present in particles having a size of greater than about 50 nm. For example, the antimicrobial metal may be particles having a size equal to or greater than about 100 nm or equal to or greater than about 200 nm or equal to or greater than about 300 nm or equal to or greater than about 400 nm or equal to or greater than about 500 nm or equal to or greater than about 600 nm or equal to or greater than about 700 nm or equal to or greater than about 800 nm or equal to or greater than about 900 nm or equal to or greater than about 1 μm. For example, the antimicrobial metal may be particles having a size up to about 100 μm or up to about 50 μm or up to about 10 μm.

The antimicrobial metal may, for example, be associated with the inorganic particulate mineral (e.g. within or at the surface of the inorganic mineral particles). For example, the antimicrobial metal may not be in solution or in suspension with a liquid medium (e.g. aqueous medium) of the composition.

In certain embodiments, the antimicrobial metal may be present on the surface of the inorganic particulate mineral. In certain embodiments, the antimicrobial metal may be adsorbed on the surface of the inorganic particulate mineral or may be embedded in the surface of the inorganic particulate mineral. In certain embodiments, the antimicrobial metal may be chemically bonded to the surface of the inorganic particulate mineral (e.g. where the inorganic particulate mineral is an alkali earth metal carbonate, the antimicrobial metal may be chemically bonded to the surface to form antimicrobial metal carbonate or where the inorganic particulate mineral is talc, mica and/or zeolite, the antimicrobial metal may be chemically bonded to the surface to from antimicrobial metal silicate).

In certain embodiments, the antimicrobial metal is incorporated within the particles of the inorganic particulate mineral. This means that the antimicrobial metal is not solely on the surface of the inorganic particulate mineral particles and at least some (e.g. all) of the antimicrobial metal is not exposed to (i.e. is not in contact with) the particle's surroundings. However, this does not preclude some of the antimicrobial metal also being present on the surface of the inorganic particulate mineral particles (e.g. as part of a coating or embedded on the surface of the inorganic particulate mineral particles (i.e. party within and partly outside of the inorganic particulate mineral particle)) or being present in solution or suspension. The antimicrobial metal may, for example, be physically and/or chemically bonded to the inorganic particulate mineral within the particles of the inorganic particulate mineral.

The antimicrobial metal may be chemically bonded to the inorganic particulate mineral. For example, the antimicrobial metal may be chemically bonded to the inorganic particulate mineral by one or more of covalent, metallic and ionic (e.g. cationic) bonds. For example, the antimicrobial metal may be chemically bonded to the inorganic particulate mineral to form an antimicrobial metal compound. The antimicrobial metal compound may, for example, have the same anion as the inorganic particulate mineral. For example, the inorganic particulate mineral may be an alkali earth metal carbonate and the antibacterial metal may be bonded to the alkali earth metal carbonate to form an antimicrobial carbonate. For example, the inorganic particulate mineral may be calcium carbonate and the antimicrobial metal bonds to the calcium carbonate to form antimicrobial metal carbonate. For example, the inorganic particulate mineral may be one or more of diatomite, talc, mica or zeolite and the antimicrobial metal may be bonded to the diatomite, talc, mica and/or zeolite to form antimicrobial metal silicate. The antimicrobial metal (e.g. antimicrobial metal compound such as antimicrobial metal carbonate or silicate) may, for example, be part of the crystal structure/matrix of the inorganic particulate mineral.

The antimicrobial metal (e.g. antimicrobial metal compound) may be physically bonded to the inorganic particulate mineral. For example, the antimicrobial metal may be physically bonded to the inorganic particulate mineral by one or more of Van der Waals forces, London dispersion forces, dipole-dipole interactions, hydrogen bonding and Debye forces (induced dipole forces). For example, particles or distinct regions of an antimicrobial metal (e.g. antimicrobial meta compound) may be physically associated with particles or distinct regions of an inorganic particulate mineral to form an aggregate, which may, for example, have the same particle size distribution features as described herein for the inorganic particulate mineral particles.

Where the antimicrobial metal is incorporated within the inorganic particulate mineral particles, the antimicrobial metal may be distributed throughout the inorganic particulate mineral particles, for example may be evenly distributed throughout the inorganic particulate mineral particles, e.g. to form a regular pattern of antimicrobial metal. For example, an antimicrobial metal compound (e.g. regions or particle of an antimicrobial metal compound), which may, for example, be formed by chemical bonding between the antimicrobial metal and the inorganic particulate mineral or may be formed as a by-product of a process for making the inorganic particulate mineral, may be evenly distributed throughout the inorganic particulate mineral particles.

Alternatively, the antimicrobial metal compound may be unevenly distributed through the inorganic particulate mineral particles. For example, the antimicrobial metal, for example an antimicrobial metal compound, may be located in the core of the inorganic particulate mineral particles. For example, the inorganic particulate mineral may be formed (e.g. precipitated) on the surface of the antimicrobial metal (e.g. antimicrobial metal compound). For example, an alkali earth metal carbonate such as calcium carbonate may be precipitated on the antimicrobial metal (e.g. antimicrobial metal compound).

Where the antimicrobial metal (e.g. antimicrobial metal compound) is located in the core of the inorganic particulate mineral particles, the inorganic particulate mineral may be chemically or physically bonded to the antimicrobial metal core or antimicrobial metal compound core. Where the core is formed of an antimicrobial metal compound, the anion of the antimicrobial metal compound may be the same as the anion of the inorganic particulate mineral. Where the core is formed of an antimicrobial metal compound, the antimicrobial metal compound may be formed by bonding an antimicrobial metal to an inorganic particulate mineral or as a by-product of a process of making the inorganic particulate mineral. The inorganic particulate mineral surrounding the antimicrobial metal compound core may, for example, be the same or different to the inorganic particulate mineral that was used to form the antimicrobial metal compound.

In certain embodiments, the composition comprises particles of an inorganic particulate mineral and particles of an antimicrobial metal compound (i.e. a mixture of an inorganic particulate mineral and an antimicrobial metal compound). The anion of the antimicrobial metal compound may, for example, be the same as the anion of the inorganic particulate mineral. For example, the inorganic particulate mineral may be an alkali earth metal carbonate and the antimicrobial metal compound may be an antimicrobial metal carbonate. For example, the inorganic particulate mineral may be talc, mica and/or zeolite and the antimicrobial metal compound may be an antimicrobial metal silicate. The antimicrobial compound may, for example, be the antimicrobial compound that would be or is formed by reacting the inorganic particulate mineral with the antimicrobial metal or would be or is formed as a by-product of a method of making the mineral. For example, the inorganic particulate mineral may be an alkali earth metal carbonate and the antimicrobial metal compound may be antimicrobial metal carbonate. For example, the inorganic particulate mineral may be one or more of talc, mica or zeolite and the antimicrobial metal compound may be an antimicrobial metal silicate. The particles of the inorganic particulate mineral and antimicrobial metal compound may, for example, be physically bonded to form an aggregate. The aggregate may, for example, have the same particle size distribution as described herein for the inorganic particulate mineral particles.

Alternatively or additionally, the antimicrobial metal may be in solution or in suspension in a liquid medium (e.g. aqueous medium) of the composition. For example, the antimicrobial metal ion may be in solution or in suspension in a liquid (e.g. aqueous) medium.

Without wishing to be bound by theory, it is believed that compositions where the antimicrobial metal is on the surface of or is incorporated within particles of the inorganic particulate mineral, release antimicrobial metal ions (e.g. silver ions) into the surrounding environment (e.g. into solution), which provide an antimicrobial effect. It is believed that the chemistry and structure of the compositions may influence the rate at which antimicrobial metal ions are released into solution.

Further Additives

The composition (e.g. aqueous suspension) may optionally further comprise other additives. For example, the composition (e.g. aqueous suspension) may further comprise one or more further optional additives which affect the pH of the composition (e.g. aqueous suspension), one or more dispersing agents, one or more thickening agents and/or one or more anti-settling agents.

The compositions disclosed herein comprising an inorganic particulate mineral (e.g. calcium carbonate such as PCC) and an antimicrobial metal may, for example, be further combined with one or more other inorganic particulate minerals, such as any inorganic particulate mineral listed above or hereinafter. Suitable inorganic particulate minerals may be selected from one or more of the following: alkaline earth metal carbonate (for example dolomite, i.e. $CaMg(CO_3)_2$), metal sulphate (for example gypsum), metal silicate, metal oxide (for example iron oxide, chromia, antimony trioxide or silica), metal hydroxide, wollastonite, bauxite, talc (for example, French chalk), mica, zinc oxide (for example, zinc white or Chinese white), titanium dioxide (for example, anatase or rutile), zinc sulphide, calcium carbonate (for example precipitated calcium carbonate (PCC), ground calcium carbonate (GCC), for example obtained from limestone, marble and/or chalk, or surface-modified calcium carbonate), barium sulphate (for example, barite, blanc fixe or process white), alumina hydrate (for example, alumina trihydrate, light alumina hydrate, lake white or transparent white), clay (for example kaolin, calcined kaolin, China clay or bentonite), zeolites and combinations thereof.

Methods of Making Inorganic Particulate Mineral Compositions

There is further provided herein a method of making any one of the compositions disclosed herein, including all embodiments thereof in all possible combinations.

The method comprises combining the inorganic particulate mineral and the antimicrobial metal. Where the composition is an aqueous slurry, the method comprises combining the inorganic particulate mineral, the antimicrobial metal and water. Where the composition comprises particles of an inorganic particulate mineral and particles of an antimicrobial metal compound, the method may comprise combining the inorganic particulate mineral and antimicrobial metal compound. Combining may, for example, be or including mixing.

In certain embodiments, the inorganic particulate mineral is in the form of a slurry and the slurry is combined (e.g. mixed) with an antimicrobial metal. For example, the inorganic particulate mineral may be a kaolin slurry which is mixed with an antimicrobial metal (e.g. silver, for example in the form of silver chloride), which may, for example, be in a solution. The antimicrobial metal may, for example, become associated with the surface of the particles of the mineral, for example by cationic attachment.

In certain embodiments, the inorganic particulate mineral is in the form of a dry mineral and the dry mineral is combined (e.g. mixed) with an antimicrobial metal. In certain embodiments, the inorganic particulate mineral may be dry kaolin which is mixed with an antimicrobial metal (e.g. silver, for example in the form of silver chloride), which may, for example, be in a solution. This mixture may, for example, then be dried to remove any water that may have been added with the antimicrobial metal. The antimicrobial metal may, for example, become associated with the surface of the particles of the mineral, for example by cationic attachment.

In certain embodiments, dry inorganic particulate mineral and dry antimicrobial metal are blended together to form an antimicrobial composition. For example, the inorganic particulate mineral may be kaolin. For example, the antimicrobial metal may be silver (e.g. in the form of silver chloride).

In certain embodiments, the inorganic particulate mineral is a synthetic mineral (i.e. is not obtained from natural sources) and the antimicrobial metal is combined with the inorganic particulate mineral before, during or after its synthesis. In certain embodiments, the inorganic particulate mineral is precipitated calcium carbonate, synthetic talc, synthetic mica or synthetic zeolite and the antimicrobial metal is combined with the inorganic particulate mineral before, during or after synthesis of the precipitated calcium carbonate, synthetic talc, synthetic mica or synthetic zeolite respectively. This may, for example, result in the formation of particles of inorganic particulate mineral having an antimicrobial metal (e.g. antimicrobial metal compound) incorporated within the particles of inorganic particulate mineral.

Thus, there is further provided herein a method of making a composition comprising an inorganic particulate mineral and an antimicrobial metal, wherein the method comprises making the synthetic inorganic particulate mineral in the presence of an antimicrobial metal. For example, there is provided herein a method of making precipitated calcium carbonate or synthetic talc in the presence of an antimicrobial metal. For example, there is provided a method of making a composition comprising an inorganic particulate mineral and an antimicrobial metal comprising forming the inorganic particulate mineral in the presence of the antimicrobial metal. For example, there is provided a method of making a composition comprising reacting slaked lime with carbon dioxide in the presence of an antimicrobial metal (e.g. antimicrobial metal salt, e.g. antimicrobial metal halide). The antimicrobial metal may, for example, be added during one or more steps of the method of making the inorganic particulate mineral. For example, the antimicrobial metal may be added completely or incrementally at various stages of the precipitation process.

The synthetic mineral (e.g. precipitated calcium carbonate) may be formed by any method known in the art, including any of the methods described above, wherein an antimicrobial metal is added to at least one step of the method.

For example, synthetic carbonate (e.g. calcium carbonate) may be formed by:
a) calcining a source of metal (e.g. alkali earth metal carbonate such as limestone);
b) slaking the calcined product in water, for example to obtain calcium hydroxide or milk of lime;
c) contacting the slaked product with a source of carbon dioxide or carbonate (e.g. sodium carbonate);
wherein an antimicrobial metal is added to at least one of steps a), b) and c).

In certain embodiments, the product of step b), e.g. milk of lime, is first contacted with ammonium chloride to give a calcium chloride solution and ammonia gas. The calcium chloride solution is then contacted with sodium carbonate (e.g. soda ash) to produce calcium carbonate.

The antimicrobial metal may, for example, be added during step b) or step c). This may, for example result in the presence of ionic antimicrobial metal (e.g. ionic silver) in solution. The antimicrobial metal ion (e.g. ionic antimicrobial metal) may then be carbonated to form antimicrobial metal (e.g. silver) carbonate.

Steps b) and/or c) may, for example, be carried out in the presence of an acid. The acid may, for example, be citric acid.

Steps b) and/or c) may, for example, be carried out at a temperature ranging from about 30° C. to about 150° C. For example, steps b) and/or c) may be carried out at a temperature ranging from about 35° C. to about 100° C., for example from about 40° C. to about 80° C., for example from about 45° C. to about 75° C., for example from about 50° C. to about 70° C., for example from about 50° C. to about 60° C. For example, steps b) and/or c) may be carried out at a temperature of about 55° C.

For example, a synthetic carbonate may be formed by reacting gypsum (calcium sulphate) with ammonium carbonate or ammonium bicarbonate in the presence of an antimicrobial metal.

For example, a synthetic carbonate may be formed by reacting calcium chloride with sodium carbonate or ammonium carbonate in the presence of an antimicrobial metal.

The antimicrobial metal used in the methods described herein may be the elemental metal, a metal ion or a compound including the metal (e.g. metal salt) or any combination thereof. For example, the antimicrobial metal may be an antimicrobial metal salt. For example, the antimicrobial metal may be a metal halide (e.g. chloride, fluoride, bromide, iodide, astatide), antimicrobial metal acetate, antimicrobial metal citrate, antimicrobial metal nitrate, antimicrobial metal nitrite, antimicrobial metal phosphate and antimicrobial metal sulphate. For example, the antimicrobial metal may be an antimicrobial metal halide or an antimicrobial metal nitrate. For example, the antimicrobial metal may be an antimicrobial metal chloride. The antimicrobial metal used in the methods described herein may, for example, not be an antimicrobial metal colloid (e.g. elemental antimicrobial metal colloid or antimicrobial metal salt colloid). The antimicrobial metal used in the methods described herein may, for example, not be a nanoparticulate antimicrobial metal colloid.

Where the antimicrobial metal is provided in the form of an antimicrobial metal compound, a greater wt % of the compound may be required to provide a desired wt % of antimicrobial metal in the composition. For example, the antimicrobial metal compound may be used in an amount ranging from about 0.01 to about 15% by weight or from about 0.1 to about 15 wt % by weight of the inorganic particulate mineral. The antimicrobial metal may be present in the final composition in an amount ranging from about 0.1 to about 10% by weight of the inorganic particulate mineral.

The antimicrobial metal may, for example, react with one of the reactants of a process for making an inorganic particulate mineral to form an antimicrobial metal compound. The antimicrobial metal compound may, for example, be present within the particles of the inorganic particulate mineral and/or on the surface of the inorganic particulate mineral and/or as a particles of antimicrobial metal compound that may or may not be physically bonded with the inorganic particulate mineral to form an aggregate). For example, where the inorganic particulate mineral is precipitated calcium carbonate, the antimicrobial metal carbonate may be formed by the reaction of the antimicrobial metal with a carbonate reactant. Where the antimicrobial metal is present in the composition in the form of antimicrobial metal compound particles, the antimicrobial metal compound may, for example, not be formed during (e.g. as a by-product) the production of the inorganic particulate mineral. For example, the antimicrobial metal compound may be obtained or provided independently to the inorganic particulate mineral.

The antimicrobial metal may, for example, react with the inorganic particulate mineral to form an antimicrobial metal compound that is present within the particles of the inorganic particulate mineral and/or on the surface of the inorganic particulate mineral and/or as a particles of antimicrobial metal compound that may or may not be physically bonded with the inorganic particulate mineral to form an aggregate.

The resultant inorganic particulate mineral compositions (i.e. comprising inorganic particulate mineral such as PCC and the antimicrobial metal or antimicrobial metal compound) may, for example, be filtered and/or dried and/or milled and/or screened and/or dewatered (e.g. by thermal or mechanical dewatering) to provide a high solids slurry. The resultant inorganic particulate mineral composition may, for example, be coated (e.g. with one or more fatty acids) as described herein.

Uses of the Inorganic Particulate Mineral Compositions

There is provided herein the use of an antimicrobial metal as an antimicrobial additive in a composition comprising inorganic particulate mineral. The term "antimicrobial" may mean that the antimicrobial metal acts to prevent or inhibit (e.g. reduce the rate of) growth of one or more microbes and/or that the antimicrobial metal acts to reduce or substantially eliminate, e.g. eliminate, microbes from the composition. This may be determined over a period of time, for example after 1 day, 2 days, 3 days, 4 days, 5 days, 6 days or 7 days. This may be determined by measuring total viable count of the composition.

The compositions comprising an inorganic particulate mineral and an antimicrobial metal may, for example, be used to prevent or inhibit the growth of one or more microbes. For example, the compositions comprising an inorganic particulate mineral and an antimicrobial metal may be used to reduce the number or substantially eliminate, e.g. eliminate, microbes, for example after 1 day, 2 days, 3 days, 4 days, 5 days, 6 days or 7 days. The compositions may, for example, impart antimicrobial properties onto any product in which it is incorporated. The compositions may, for example, have an antimicrobial effect on any material into or onto which it is applied.

The compositions comprising an inorganic particulate mineral and an antimicrobial metal may, for example, be used an additive or filler in a polymer composition. For example, the composition may be incorporated into a coating composition (e.g. on its own or with other minerals), which may, for example, comprise a polymeric binder and the composition. The coating compositions may, for example, be used to coat or fill paper (all forms of paper, including board, such as, for example, white-lined board and linerboard, cardboard, paperboard, coated board, and the like), plastic and/or metal substrates. For example, the coating compositions may be used to coat substrates for use in packaging, for example for use in food packaging. The compositions may, for example, be used in coatings on personal grooming items such as hair straighteners or curling irons. The compositions comprising an inorganic particulate mineral and an antimicrobial metal may, for example, be used in adhesives and/or sealants and/or rubbers and/or joint compounds and/or floor coverings and/or wall coverings and/or ceiling coverings and/or roof coatings and/or packaging and/or personal care items (e.g. cosmetics, foot powder) and/or paints and/or coatings and/or machining fluids. The compositions comprising an inorganic particulate mineral and an antimicrobial metal may, for example, be used in textiles, for example for garments and/or shoes.

Thus, there is provided herein polymer compositions (e.g. polymeric articles) comprising a polymer and a composition comprising an inorganic particulate mineral and an antimicrobial metal as described herein. For example, there is provided a coating composition comprising a polymeric binder and a composition comprising an inorganic particulate mineral and an antimicrobial metal as described herein.

For example, there is provided an adhesive and/or a sealant and/or a rubber and/or a joint compound and/or a floor covering and/or a wall covering and/or a ceiling covering and/or a roof coating and/or packaging and/or a personal care item (e.g. cosmetic or foot powder) and/or a paint and/or a coating composition and/or a machining fluid comprising a composition comprising an inorganic particulate mineral and an antimicrobial metal. For example, there is provided a textile material comprising a composition comprising an inorganic particulate mineral and an antimicrobial metal.

The compositions comprising an inorganic particulate mineral and an antimicrobial metal as described herein may, for example, be used in purification or filtration (e.g. active filtration) systems. For example, the compositions may be used in air or water purification or filtration (e.g. active filtration) systems. The use of these compositions may, for example, make the air or water suitable for animal, e.g. human, consumption.

The compositions comprising an inorganic particulate mineral and an antimicrobial metal may, for example, be used in agriculture. For example, the compositions comprising an inorganic particulate mineral and an antimicrobial metal as described herein may be used for protection of plants (e.g. crops) from one or more microbes.

The compositions comprising an inorganic particulate mineral and an antimicrobial metal may, for example, be used in oilfield applications. For example, the compositions comprising an inorganic particulate mineral and an antimicrobial metal may be used in wellbore or drilling fluids.

The compositions comprising an inorganic particulate mineral and an antimicrobial metal may, for example, be used in machining fluids such as coolants, lubricants, cutting fluids and metalworking fluids.

The compositions comprising an inorganic particulate mineral and an antimicrobial metal may, for example, be used in personal care or personal hygiene products. For example, the compositions may be used in cosmetics (e.g. make-up, moisturizers), hair products, hair removal products, body wash, body powders such as foot powders, deodorants and anti-perspirants or oral hygiene products (e.g. toothpaste).

The compositions comprising an inorganic particulate mineral and an antimicrobial metal as described herein may, for example, be used in animal feed. Thus, provided herein is an animal feed composition comprising a composition comprising an inorganic particulate mineral and an antimicrobial metal as described herein. The animal feed may, for example, inhibit growth of microbes or reduce the number of microbes in the animal, for example in animal products (e.g. meat, milk, eggs). This may, for example, extend the shelf life of animal products (e.g. meat, milk, eggs). Incorporation of a composition comprising an inorganic particulate mineral and an antimicrobial metal into animal feed may, for example, provide an animal product with a particular colour, which may, for example, change over time thus indicating shelf life. For example, the animal feed may provide egg shell with a pale blue/grey colour. The animal feed may, for example, be chicken feed, cattle feed, goat feed, sheep feed, horse feed, pig feed, deer feed, rabbit feed, cat feed or dog feed.

The compositions comprising an inorganic particulate mineral and an antimicrobial metal as described herein may, for example, be used to form a surface-mineralized substrate. That is, the compositions comprising an inorganic particulate mineral and an antimicrobial metal as described herein may be embedded into a surface region of a substrate and/or may be attached to the surface of a substrate to form a surface-mineralized substrate. By "surface-mineralized" is meant that the substrate is capable of having an inorganic particulate material (i.e., mineral) having an antibacterial capability embedded in a surface region of the substrate or attached to a surface of the substrate (e.g. by electrostatic interactions) by applying the inorganic particulate material having an antibacterial capability to the surface of the substrate under suitable conditions. Thus, provided herein is a surface-mineralized substrate comprising a substrate having a composition comprising an inorganic particulate mineral and antimicrobial metal as described herein embedded into a surface region of said substrate and/or attached to the surface of the substrate.

As used herein, the term "surface region" means a region extending from the surface of the substrate into the body of the substrate. This region may, for example, comprise up to 10% of the thickness of the substrate, for example up to 9% or up to 8% or up to 7% or up to 6% or up to 5% or up to 4% or up to 3% or up to 2% or up to 1% of the thickness of the substrate. In certain embodiments, the extent of the surface region is such that at least a portion of the composition is partially, but not wholly, embedded in the surface of the substrate. In certain embodiments, the surface region is a region which extends from the surface into the body of the substrate by a distance (i.e., measured perpendicular to the plane of the surface at the measurement point) of no more than about 20 µm, for example, no more than about 15 µm, or more than about 10 µm, or no more than about 5 µm, or no more than about 2 µm, or no more than about 1 µm.

The composition comprising inorganic particulate mineral and antimicrobial metal may be partially or wholly embedded in the surface region. By "partially" is meant that a portion of the inorganic particulate and/or individual particles thereof are not wholly covered in the matrix material, e.g., polymer, of the substrate. In certain embodiments, at least a portion of the inorganic particulate material and/or individual particles thereof are partially embedded in the surface region such that they are exposed to the external environment. In certain embodiments, at least a portion of the inorganic particulate and/or individual particles are sized such that they are at least partially exposed to the external environment following application to the surface of the substrate. In embodiments in which the inorganic particulate material having an antibacterial capability is partially embedded and/or attached to the surface of the substrate, a major proportion (i.e., at least 50%) of the total surface area of the inorganic particulate material may be exposed to the external environment following application to the surface of the substrate.

For the avoidance of doubt, the composition comprising inorganic particulate mineral and antimicrobial metal which is embedded in a surface region of the substrate or is attached to a surface of the substrate is not comprised within a coating or coating layer or film layer applied to a position on a surface of the substrate. Further, the composition comprising inorganic particulate mineral and antimicrobial metal is not prepared as a coating by making a dispersion (e.g., a liquid or fluid dispersion) of the composition in a curable or other type of coating which is then applied onto the surface of a substrate. In certain embodiments, the composition comprising inorganic particulate mineral and antimicrobial metal is not prepared as a fluid which is then applied to the substrate.

Advantageously, in certain embodiments, the substrate is surface-mineralized during manufacture of the substrate, e.g., following extrusion of a polymeric substrate.

The surface-mineralized substrate may be made by a method comprising applying a composition comprising inorganic particulate mineral and antimicrobial metal as described herein to the surface of a substrate, wherein the substrate has a surface region which is embeddable with the composition and/or a surface to which the composition is attachable, and wherein the composition becomes embedded in the surface region of the substrate and/or attached to the surface of the substrate upon further processing.

In embodiments in which the substrate is a polymeric substrate, for example, a plastic substrate, the composition comprising inorganic particulate mineral and antimicrobial metal as described herein may be applied during manufacture of the substrate or following forming of the polymeric substrate, for example, during any suitable plastics shaping operation including compression molding, injection molding, thermoforming, calendaring and extrusion.

In such embodiments, the composition comprising inorganic particulate mineral and antimicrobial metal as described herein may be applied to a surface of the substrate while the surface is in a softened state. For example, in a compression molding, injection molding or extrusion process, the composition may be applied following molding/extrusion but before the molded/extruded piece has fully cooled. In other words, the temperature of the surface region of the substrate is such that the composition becomes embedded in the surface region or at least attached to the surface. For example, the surface region of the substrate may be at a temperature at or above the melting point of the polymeric material of which the substrate is formed. In a laminate or layered substrate, the outermost, surface facing layer of polymeric material may have a melting temperature which is lower than the innermost layer or layers of the substrate, therefore providing an operating window in which the innermost layer or layers remain substantially solid whilst the surface region of the outermost layer is surface mineralized. Further processing of the substrate, e.g., by cooling and/or by the application of pressure to the surface (e.g., by using a roller) "locks-in" the composition.

In other embodiments, the molded/extruded piece may be fully cooled and then heat applied to a surface portion to "re-soften" e.g., melt, the surface region and then a composition comprising inorganic particulate mineral and antimicrobial metal as described herein is applied to the surface. Additionally or alternatively, the composition may be attached to a surface of the molded/extruded piece without having to soften or re-soften the surface, for example, by electrostatic attachment, between a surface of the substrate and the composition. In certain embodiments, the composition is attached to the surface electrostatically, e.g., by an electrostatic pinning method. Further, in certain embodiments, the composition may be positively or negatively charged, or modified such that it is positively or negatively charged, whilst the substrate is oppositely charged (or modified such that it is oppositely charged). This may enhance an even distribution of the composition when applied and also enhance adherence of the composition to the surface of the surface prior to an embedding step.

In certain embodiments, the substrate is a thermoforming film and the composition comprising inorganic particulate mineral and antimicrobial metal as described herein is applied to the surface of the polymeric film in a thermoforming process. Such a process for manufacturing packaging items is usually carried out using a roll of film, for example, an indexed roll of film, typically but not exclusively in a semi-continuous process, with a roll of film loaded at one end of the process and thermoformed containers, e.g., trays, produced at the end of the process. The trays are normally die cut from the film, and stacked at the end of the process. In certain embodiments, the process is a continuous process. In other embodiments, the process may be a batch process.

Typical steps in a thermoforming process are: 1) index film to heating position, 2) heat film (e.g., by IR), 3) index over mould, 4) pre-stretch, 5) vacuum or overpressure applied, 6) cooling, 7) index over die cutting, 8) die cutting, 9) ejection and stacking, and 10), index of matrix waste to rewind.

In certain embodiments, the composition comprising inorganic particulate mineral and antimicrobial metal is applied to the thermoforming film prior to heating (which may be carried by IR treatment, but other heating techniques may be used), e.g., between steps 1) and 2) above. Alternatively, the composition may be applied following film heating, e.g., between steps 2) and 3). The application of the composition can be done with or without masking, or by using automated (e.g., computerised) control to prevent or ameliorate the composition falling in certain areas. An advantage of such a process is that once the thermoformed product is formed, the surface-mineralization is present at desired areas, for example, the base of a tray, and may not interfere with sealing or film clarity. In addition or alternatively, the composition can be electrostatically pinned to the plastic substrate. The thermoforming process may be completed with a prestretcher that applies pressure (and optionally additional temperature) into a desired area (e.g., the base of a tray) which facilitates embedding of the composition into the surface region of the substrate, prior to vacuum or over pressure stretching the thermoforming film into the corner regions of the mould.

In certain embodiments in which the film is printed then the surface-mineralization process can be carried out after printing and be done in register to the print (i.e., the composition comprising inorganic particulate mineral and antimicrobial metal is applied to locate and register at defined areas of the substrate). An eye mark or electric eye may be used to register the application of the composition to the desired area(s). In this way, the composition may be applied only to the back of areas where there is already print on the front side or encapsulated in a laminated film. In this way the composition may not adversely affect the clarity of the film as they are hidden by the print.

In certain embodiments, the composition comprising inorganic particulate material and antimicrobial metal is itself heated prior to application, meaning that no heat, or at least less heat, may need to be applied directly to the thermoforming film, or to the injected/extruded substrate. The composition may need to be heated to a temperature greater than the melting temperature of the polymer to facilitate embedding on contact with the surface of the polymeric substrate. As with other methods of application, pressure may be applied following application (e.g., by a prestrecher as used in a thermoforming process, or using an optionally heated roller) to further enhance the embedding of the composition into the surface region of the substrate.

For paper products, textiles and nonwovens and the like, the application of the composition comprising inorganic particulate mineral and antimicrobial metal may be applied during the forming process, in many ways analogously to polymeric substrate embodiments described above. For example, during manufacture of nonwovens, the composition may be applied prior to, during, or after, a final bonding step, for example, by spraying or blowing the composition at the emerging fibres or by dragging the emerging fibres through the composition. Paper products may be made by a similar process, for example, by applying (e.g., by spraying, blowing or dragging) the composition to emerging fibres during manufacture of paper, followed by a finishing step, such as calendaring or supercalendaring step, to enhance the embedding of the composition into the surface region of the paper web.

According to any of the methods described above, the composition comprising inorganic particulate mineral and antimicrobial metal may be applied by an suitable means of application. In certain embodiments, the composition is applied by spraying and/or by gravimetric application, for example, using an offset sprayer/powder sprayer or a gravimetric feeder, or a combination thereof (e.g., a gravimetric feeder feeding a sprayer which applies the composition to the surface of the substrate). Current manufacturing apparatus could be relatively easily adapted for carrying out the methods described herein by incorporating a sprayer and optionally a gravimetric feeder.

Use of a surface-mineralized substrate may for example, improve the antimicrobial activity of the substrate for use in or as packaging for fresh produce (e.g. uncooked meat). This may, for example, improve the shelf-life or consumer-appeal of the fresh produce.

The total amount of the composition comprising inorganic particulate mineral and antimicrobial metal embedded in a surface region and/or attached to a surface of the substrate is generally no more than about 5% by weight, based on the total weight of the surface-mineralized substrate. In certain embodiments, the total amount of the composition comprising inorganic particulate mineral and antimicrobial metal embedded in a surface region and/or attached to a surface of the substrate is no more than about 4% by weight or no more than about 3% by weight or no more than about 2% by weight or no more than about 1.5% by weight or no more than about 1% by weight or no more than about 0.5% by weight or no more than about 0.25% by weight or no more than about 0.1% by weight of the total weight of the surface-mineralized substrate.

The amount of the composition comprising inorganic particulate mineral and antimicrobial metal in the surface region of the surface-mineralized substrate and/or attached to a surface of the surface-mineralized substrate may be determined by ashing the surface-mineralized substrate.

In certain embodiments, the surface-mineralized substrate comprises an amount of inorganic particulate material other than in the surface region and/or attached to a surface thereof, for example, an amount of inorganic particulate that is incorporated during compounding of the substrate. In certain embodiments, the surface-mineralized substrate does not contain any inorganic particulate material other than in the surface region and/or attached to a surface thereof.

In certain embodiments, the substrate is a polymeric substrate, for example, a plastic, which is, or may be processed into, and article selected from articles for building and construction, household items and furnishings, electrical and electronic parts, coatings and laminates, transportation and recreation, food contact items and water contact items, films, coextrusion films, and exterior and interior automotive parts.

In certain embodiments, the substrate is a polymer selected from aliphatic and aromatic polyesters, such as polyethylene terephthalate (PET), polybutylene terephthalate, polyethylene isophthalate, polyhexamethylene terephthalate, polylactic acid, polyglycolic acid, and liquid crystalline polymers for high performance resins and fibers; polyester block copolymers; aliphatic and aromatic polyamides, such as nylon 6, nylon 66, nylon 610, nylon 11, nylon 12, nylon 1212, poly-p-phenylene terephthalamide, poly-m-phenylene isophthalamide; copolymerised polyamides; polyolefins such as polyethylene, polypropylene, and copolymers thereof; vinyl polymers such as polystyrene, polyacrylonitrile, polyvinylalcohol, polyvinyl acetate, polyvinylchloride, polyvinylidene chloride, ABS resins, and acrylic resins; copolymers of ethylene and vinyl acetate; fluorocarbon polymers such as polytetrafluoroethylene, polyvinylidene fluoride and polyvinyl fluoride; polyurethanes; segmented polyurethane elastomers, spandex or elastane elastomers; polyethers such as polyacetals; polyketones such as polyetherether ketone (PEEK) and polyether ketoneketone (PEKK); polyether and polyester block polymers; polysulfides; polysulfones: polysiloxanes such as polydimethyl siloxane; polycarbonates; thermosetting synthetic polymers such as phenol-formaldehyde copolymer, polyurethane, polyesterurethane, polyetherurethane, polyetherurethaneurea, and polyesterurethaneurea; natural polymers such as cellulosics, cotton and wool; and, regenerated or semi-synthetic polymers such as rayon, cuprammonium rayon, acetate rayon, triacetate rayon, reconstituted silk and polysaccharides. Copolymers, terpolymers, and blends of the polymer species listed are also contemplated.

In certain embodiments, at least a portion of the polymer is recycled polymer, for example, recycled post-consumer polymer waste. In certain embodiments, substantially all of the thermoplastic polymer is recycled. In certain embodiments, the recycled polymers are derived from polymer waste, for example, post-consumer polymer waste, post-industrial polymer waste, and/or post-agricultural waste polymer. In certain embodiments, the polymers are recycled post-consumer polymer waste.

In certain embodiments, the substrate is a polymeric film or laminate, for example, a polymeric film or film that may be processed into a container and/or tray and/or film for food grade packaging, for example, packaging for fresh produce such as, but not limited to, uncooked meats such as poultry, e.g., chicken, and cooked meats. In certain embodiments, the polymeric container or tray is formed of polypropylene or PET. Such containers and trays may be sealed with a flexible film of polyethylene or a polyester laminate. In certain embodiments, the substrate is a thermoforming film that may be processed into a container or tray for fresh produce. As discussed below, advantageously surface mineralization may be carried out during the thermoforming process.

In certain embodiments, the substrate is a cellulose-based substrate, for example, a paper product or textile.

In certain embodiments, the substrate is a nonwoven substrate. Surface-mineralized nonwoven substrates include products uses alone or as components of apparel, home furnishings, health care, engineering, industrial and consumer goods. Nonwoven products include solation gowns, surgical gowns, surgical drapes and covers, surgical masks, surgical scrub suits, caps, diaperstock, feminine hygiene, and other absorbent materials (e.g., sanitary wipes, baby wipes), carpet backing, primary and secondary, composites marine sail laminates, tablecover laminates, chopped strand mat, backing/stabilizer for machine embroidery, insulation, acoustic insulation for appliances, automotive components, and wall-paneling, pillows, cushions, mattress cores, and upholstery padding batting in quilts or comforters, consumer and medical face masks, mailing envelopes, tarps, tenting and transportation (lumber, steel) wrapping disposable clothing (foot coverings, coveralls), weather resistant house wrap, and cleanroom wipes. In certain embodiments, the nonwoven substrate is a wipe suitable for household use, for example, a sanitary wipe or baby wipe.

Exemplary applications include, but are not limited to, animal feed, cosmetic formulations, paints, inks, home care products, animal care products, building materials, paper products, fabric products (e.g., textiles), products for personal and work hygiene, contact lenses, chromatography materials, medical equipment, protective topicals, pharmaceutical and especially dermatological formulations, lacquers, coatings, polymers, and plastics. Additional exemplary applications include, but are not limited to, adhesives and sealants, antimicrobial cleansers, soaps, disinfectants, anti-fouling and antimicrobial paints for inside and outside use, anti-foulant marine coatings, animal husbandry, antimicrobial wallpapers, antimicrobial dressings and plasters, prostheses and bone cement with antimicrobial activity, dental fillings, dental prostheses, formulations against gastrointestinal infections, active coal, antimicrobial cat litter, air conditioning (e.g., filters and ducts), air inflated construction (e.g., air halls), agricultural and mulch films, all purpose adhesives, appliances and equipment, appliance adhesives and sealants, aprons, artificial leather, artificial plants, artificial wood, and plastic lumber, Astroturf, automobile parts, automotive and truck upholstery, awnings, bags, bandages, barrier fabrics, bathroom accessories, bathtubs, bathtub cement, bedding, beverage dispensers, bibs, boats, boat covers, book covers, bottles, brush bristles, brush handles, brooms, building components (e.g., walls, wallboard, floors, concrete, siding, roofing, shingles, hardware, carpet cleaner, ceilings and commercial and industrial applications), cable sheathing, caps (e.g., hats), cardboard, carpet and carpet underlay, caster wheels, cat litter, clinical thermometers, coats, compact discs, convertible tops, cookware, coolers, cooling towers, cooling water, counter and table tops, conveyor belts, countertops, credit cards, crates (for both food and non-food uses), cups, currency, curtains, cushion pads, cutting boards, decking, dishes, dish cloths, dishwasher components, diving equipment or snorkels, drainage sewer pipe, draperies, dry-film paints, exercise equipment, equipment for slaughterhouses or creameries or diaries, equipment for gyms, saunas or massages, fan blades, fiberfill, filters, fittings, fences, floor coverings, floor and carpet baking, flooring, foam (e.g., for cushions and mattresses), food preparation appliances, food and beverage processing equipment, food and drink containers, storage and bags, food handling equipment, food packaging, food and meat crates, food trays and covers, food wrap, footwear (including, for example, boots, sports equipment, and tools), fruit and vegetable brushes, fruit crates, furniture, garbage bags, garbage cans, garment bags, gaskets, general purpose containers, gloves, gowns (e.g., medical and consumer), grease traps, rigid greenhouses, greenhouse films, grout and joint compound, heating, ventilation and air conditioning, hospital surface and medical instrument disinfection, hoses, ice-making equipment and trays, in-can paints, incontinence care products, indoor and outdoor furniture, industrial equipment, inflatable bed, insulation for wire and cable, insulators, intimate apparel, jacket liners, janitorial equipment, kitchen and bathroom hardware, kitchen sinks and fixtures, kitchen towels, laminate and tile adhesives, laying batteries, life vests, liners, mats, mattress cover pads and filing, mattress adhesives, medical and dental apparel, metal working fluids, mineral slurries, mobile homes, mobile toilets, mops, money, natural and synthetic fibers and fabrics, nonwoven fabrics, oilfield, outerwear, packaging, pallets, paper products (e.g., wipes, tissues, wall coverings, towels, book covers, mulch), pillow covers, pipes, pipe sealant and insulating materials, plaster, plastics, plastic films, plates and utensils, playground equipment, plumbing supplies and fixtures (including, for example, toilet bowl seats), plumbing adhesives and sealants, pool liners, process vessels, protective covers, recreational water, resins, refrigerator components, roofing sheets, membranes, shingles and flashing, ropes, rugs, sales counter, sails, sanitary pipes, sealers, sealing compounds for bathrooms, kitchens or glass, sheets and blankets, shoes, shoe insoles, shower curtains, shower tubs, siding for housing, silage wrap, silos, sinks, siphons, skylights, sleeping bags, sleepwear, socks and hosiery, sponges, sprinkler, sportswear and sports equipment, storage containers, stucco, sun roof, sun shades, synthetic latex polymers, napkins, tanks, tape, tarps, telephone boxes or public phones, tents and other outdoor equipment, ticking (e.g., for mattress pillows), tiles, tile grout, toothbrush handle and bristles, toilet paper and handkerchiefs, toilet blocks and cleaners, towels, toothbrush tumbler, toys, trim for outerwear and garments, trunk liners, tubing, umbrellas, uniforms, undergarments, upholstery, vacuum cleaner bags, wall and floor covering, wallpaper, waste bags, water tanks, waste containers, water treatment, water and ice handling equipment and filters, wet suits, wipes, wire and cable, wood, and wood filled plastics.

In certain application areas, enhanced biocidal or antimicrobial activity may be useful in several stages of processing. In one embodiment, the compositions according to the present invention can be stored in the form of Masterbatches for a period of time, without substantial risk of contamination of the Masterbatch with microorganisms. The skilled artisan recognizes that such a Masterbatch can be processed in the same way as known Masterbatches, or in processing methods hereafter discovered. The treated Masterbatches may be useful in, for example, building and construction, household, items and furnishings, electrical and electronics parts, apparel, textiles and fabrics, coatings and laminates, transportation and recreation, adhesives, sealants and grouts, food contact items and water contact items (e.g., plastic bottles and bottle caps), films, coextrusion films, and exterior and interior automotive parts.

Exemplary plastics and polymers from which the articles or surface-mineralized substrates may be fabricated comprising a composition according to the present invention include synthetic, natural, and semisynthetic organic polymers. Examples of polymers include, but are not limited to: aliphatic and aromatic polyesters, such as polyethylene terephthalate, polybutylene terephthalate, polyethylene isophthalate, polyhexamethylene terephthalate, polylactic acid, polyglycolic acid, and liquid crystalline polymers for high performance resins and fibers; polyester block copolymers; aliphatic and aromatic polyamides, such as nylon 6, nylon 66, nylon 610, nylon 11, nylon 12, nylon 1212, poly-p-phenylene terephthalamide, poly-m-phenylene isophthalamide; copolymerised polyamides; polyolefins such as polyethylene, polypropylene, and copolymers thereof; vinyl polymers such as polystyrene, polyacrylonitrile, polyvinylalcohol, polyvinyl acetate, polyvinylchloride, polyvinylidene chloride, ABS resins, and acrylic resins; copolymers of ethylene and vinyl acetate; fluorocarbon polymers such as polytetrafluoroethylene, polyvinylidene fluoride and polyvinyl fluoride; polyurethanes; segmented polyurethane elastomers, spandex or elastane elastomers; polyethers such as polyacetals; polyketones such as polyetherether ketone (PEEK) and polyether ketoneketone (PEKK); polyether and polyester block polymers; polysulfides; polysulfones: polysiloxanes such as polydimethyl siloxane; polycarbonates; thermosetting synthetic polymers such as phenol-formaldehyde copolymer, polyurethane, polyesterurethane, polyetherurethane, polyetherurethaneurea, and polyesterurethaneurea; natural polymers such as cellulosics, cotton and wool; and, regenerated or semi-synthetic polymers such as rayon, cuprammonium rayon, acetate rayon, triacetate rayon, reconstituted silk and polysaccharides. Copolymers, terpolymers, and blends of the polymer species listed are also contemplated.

The following numbered paragraphs define particular embodiments of the present invention:

1. A composition comprising an inorganic particulate mineral and an antimicrobial metal, wherein the antimicrobial metal is incorporated within the particles of the inorganic particulate mineral and/or wherein the antimicrobial metal is present on the surface of the inorganic particulate mineral.
2. The composition of paragraph 1, wherein the inorganic particulate mineral has a steepness factor of at least about 10.
3. The composition of paragraph 1 or 2, wherein the inorganic particulate mineral has a steepness factor ranging from about 10 to about 90.
4. The composition of any one of paragraphs 1 to 3, wherein the inorganic particulate mineral does not comprise pores, for example does not comprise pores in which the antimicrobial metal may be deposited.
5. The composition of any one of paragraphs 1 to 4, wherein the inorganic particulate mineral is selected from the group consisting of alkali earth metal carbonate, kaolin, talc, mica, zeolite and combinations thereof.
6. The composition of any one of paragraphs 1 to 5, wherein the inorganic particulate mineral is calcium carbonate, for example precipitated calcium carbonate (PCC).
7. The composition of any one of paragraphs 1 to 6, wherein the inorganic particulate mineral is not coral sand and/or is not derived from coral sand.
8. The composition of any one of paragraphs 1 to 7, wherein the inorganic particulate mineral is synthetic, for example is synthetic calcium carbonate (e.g. PCC), synthetic talc, synthetic mica, synthetic zeolite or combinations thereof.
9. The composition of any one of paragraphs 1 to 8, wherein at least about 90% of particles of the inorganic particulate mineral are smaller than 5 microns.
10. The composition of any one of paragraphs 1 to 9, wherein at least about 50% of particles of the inorganic particulate mineral are smaller than 2 microns.
11. The composition of any one of paragraphs 1 to 10, wherein the composition is an aqueous slurry.
12. The composition of paragraph 11, wherein the aqueous slurry has a solids content of at least about 50 wt %, for example at least about 60 wt %.
13. The composition of paragraph 11 or 12, wherein the aqueous slurry has a Brookfield viscosity equal to or less than about 1200 mPa·s.
14. The composition of any one of paragraphs 1 to 13, wherein the antimicrobial metal is selected from the group consisting of silver, cobalt, nickel, copper, iron, mercury, lead, zinc, zirconium, molybdenum, bismuth, gold, aluminium, magnesium, niobium, silicon, tantalum, hafnium, lanthanum, tungsten, calcium, titanium, vanadium, cerium, strontium, tin, lithium and combinations thereof, for example wherein the antimicrobial metal is silver.
15. The composition of any one of paragraphs 1 to 14, wherein the antimicrobial metal is present in the composition in an amount ranging from about 0.1% to about 10%, for example from about 0.2% to about 5%, by weight of the inorganic particulate mineral.
16. The composition of any one of paragraphs 1 to 17, wherein the antimicrobial metal is chemically bonded to the inorganic particulate mineral.
17. The composition of paragraph 16, wherein the inorganic particulate mineral is or comprises an alkali earth metal carbonate and the antimicrobial metal is bonded to the inorganic particulate mineral to form antimicrobial metal carbonate.
18. The composition of paragraph 16, wherein the inorganic particulate mineral is or comprises one or more of talc, mica or zeolite and the antimicrobial metal is bonded to the inorganic particulate mineral to form antimicrobial metal silicate.
19. The composition of any one of paragraphs 1 to 18, wherein the antimicrobial metal is physically bonded to the inorganic particulate mineral.
20. The composition of paragraph 19, wherein the antimicrobial metal is physically bonded to the inorganic particulate mineral by one or more of Van der Waals forces, London dispersion forces, dipole-dipole interactions, hydrogen bonding and Debye force (induced dipole).
21. The composition of any one of paragraphs 1 to 20, wherein the antimicrobial metal is distributed throughout, for example evenly distributed throughout, the particles of the inorganic particulate mineral.
22. The composition of any one of paragraphs 1 to 21, wherein the antimicrobial metal is positioned at the core of the particles of the inorganic particulate mineral.
23. The composition of any one of paragraphs 1 to 22, wherein the composition has a toxic effect on one or more microbes.
24. The composition of any one of paragraphs 1 to 23, wherein the composition is substantially devoid, for example devoid, of biocide.
25. The composition of any one of paragraphs 1 to 24, wherein the composition is substantially devoid, for example devoid, of microbes.
26. A composition comprising calcium carbonate and an antimicrobial metal, wherein the calcium carbonate does not comprise pores, for example does not comprise pores in which the antimicrobial metal is deposited, and/or wherein the calcium carbonate is not coral sand and/or is not derived from coral sand.
27. The composition of paragraph 26, wherein the calcium carbonate is not coral sand and/or is not derived from coral sand and/or wherein the calcium carbonate does not comprise pores, for example does not comprise pores in which the antimicrobial metal is deposited.
28. The composition of paragraph 26 or 27, wherein the calcium carbonate is synthetic, for example is precipitated calcium carbonate.
29. The composition of any one of paragraphs 26 to 28, wherein the calcium carbonate has a steepness factor of at least about 10, for example at least about 20.
30. The composition of any one of paragraphs 26 to 29, wherein the calcium carbonate has a steepness factor ranging from about 10 to about 90.

31. The composition of any one of paragraphs 26 to 30, wherein at least about 90% of the calcium carbonate particles are smaller than 5 microns.
32. The composition of any one of paragraphs 26 to 31, wherein at least about 50% of the calcium carbonate particles are smaller than 2 microns.
33. The composition of any one of paragraphs 26 to 32, wherein the composition is an aqueous slurry.
34. The composition of paragraph 33, wherein the aqueous slurry has a solids content of at least about 50 wt %, for example at least about 60 wt %.
35. The composition of paragraph 33 or 34, wherein the aqueous slurry has a Brookfield viscosity equal to or less than about 1200 mPa·s.
36. The composition of any one of paragraphs 26 to 35, wherein the antimicrobial metal is selected from the group consisting of silver, cobalt, nickel, copper, iron, mercury, lead, zinc, zirconium, molybdenum, bismuth, gold, aluminium, magnesium, niobium, silicon, tantalum, hafnium, lanthanum, tungsten, calcium, titanium, vanadium, cerium, strontium, tin, lithium and combinations thereof, for example wherein the antimicrobial metal is silver.
37. The composition of any one of paragraphs 26 to 36, wherein the antimicrobial metal is present in the composition in an amount ranging from about 0.1% to about 10%, for example from about 0.2% to about 5%, by weight of the calcium carbonate.
38. The composition of any one of paragraphs 26 to 37, wherein the antimicrobial metal is incorporated within the particles of the calcium carbonate.
39. The composition of any one of paragraphs 26 to 38, wherein the antimicrobial metal is chemically bonded to the calcium carbonate.
40. The composition of paragraph 39, wherein the antimicrobial metal is chemically bonded to the calcium carbonate to form an antimicrobial metal carbonate.
41. The composition of any one of paragraphs 27 to 40, wherein the antimicrobial metal is physically bonded to the calcium carbonate.
42. The composition of paragraph 41, wherein the antimicrobial metal is physically bonded to the calcium carbonate by one or more of Van der Waals forces, London dispersion forces, dipole-dipole interactions, hydrogen bonding and Debye force (induced dipole).
43. The composition of any one of paragraphs 27 to 42, wherein the antimicrobial metal (e.g. the antimicrobial metal carbonate) is distributed, for example evenly distributed, throughout the particles of the inorganic particulate mineral.
44. The composition of any one of paragraphs 27 to 43, wherein the antimicrobial metal (e.g. the antimicrobial metal carbonate) is positioned at the core of the inorganic particulate mineral particles.
45. The composition of any one of paragraphs 27 to 44, wherein the composition has a toxic effect on one or more microbes.
46. The composition of any one of paragraphs 27 to 45, wherein the composition is substantially devoid, for example devoid, of biocide.
47. The composition of any one of paragraphs 27 to 46, wherein the composition is substantially devoid, for example devoid, of microbes.
48. A composition comprising precipitated calcium carbonate and an antimicrobial metal.
49. The composition of paragraph 48, wherein the precipitated calcium carbonate has a steepness factor of at least about 10, for example at least about 20.
50. The composition of paragraph 48 or 49, wherein the precipitated calcium carbonate has a steepness factor ranging from about 10 to about 90.
51. The composition of any one of paragraphs 48 to 50, wherein at least about 90% of the precipitated calcium carbonate particles are smaller than 5 microns.
52. The composition of any one of paragraphs 48 to 51, wherein at least about 50% of the precipitated calcium carbonate particles are smaller than 2 microns.
53. The composition of any one of paragraphs 48 to 52, wherein the composition is an aqueous slurry.
54. The composition of paragraph 53, wherein the aqueous slurry has a solids content of at least about 50 wt %, for example at least about 60 wt %.
55. The composition of paragraph 53 or 54, wherein the aqueous slurry has a Brookfield viscosity equal to or less than about 1200 mPa·s.
56. The composition of any one of paragraphs 48 to 55, wherein the antimicrobial metal is selected from the group consisting of silver, cobalt, nickel, copper, iron, mercury, lead, zinc, zirconium, molybdenum, bismuth, gold, aluminium, magnesium, niobium, silicon, tantalum, hafnium, lanthanum, tungsten, calcium, titanium, vanadium, cerium, strontium, tin, lithium and combinations thereof, for example wherein the antimicrobial metal is silver.
57. The composition of any one of paragraphs 48 to 56, wherein the antimicrobial metal is present in the composition in an amount ranging from about 0.1% to about 10%, for example from about 0.2% to about 5%, by weight of the precipitated calcium carbonate.
58. The composition of any one of paragraphs 48 to 57, wherein the antimicrobial metal is incorporated within the particles of the precipitated calcium carbonate.
59. The composition of any one of paragraphs 48 to 58, wherein the antimicrobial metal is chemically bonded to the precipitated calcium carbonate.
60. The composition of paragraph 59, wherein the antimicrobial metal is chemically bonded to the precipitated calcium carbonate, for example to form an antimicrobial metal carbonate.
61. The composition of any one of paragraphs 48 to 60, wherein the antimicrobial metal is physically bonded to the precipitated calcium carbonate.
62. The composition of paragraph 61, wherein the antimicrobial metal is physically bonded to the precipitated calcium carbonate by one or more of Van der Waals forces, London dispersion forces, dipole-dipole interactions, hydrogen bonding and Debye force (induced dipole).
63. The composition of any one of paragraphs 48 to 62, wherein the composition has a toxic effect on one or more microbes.
64. The composition of any one of paragraphs 48 to 63, wherein the composition is substantially devoid, for example devoid, of biocide.
65. The composition of any one of paragraphs 48 to 64, wherein the composition is substantially devoid, for example devoid, of microbes.
66. A composition comprising particles of an inorganic particulate mineral and particles of an antimicrobial metal compound.
67. The composition of paragraph 66, wherein the inorganic particulate mineral and/or particles of antimicrobial metal compound has/have a steepness factor of at least about 10, for example at least about 20.
68. The composition of paragraph 66 or 67, wherein the inorganic particulate mineral and/or particles of antimicrobial metal compound has/have a steepness factor ranging from about 10 to about 90.
69. The composition of any one of paragraphs 66 to 68, wherein the inorganic particulate mineral does not comprise pores, for example does not comprise pores in which the antimicrobial metal may be deposited.
70. The composition of any one of paragraphs 66 to 69, wherein the inorganic particulate mineral is selected from the group consisting of alkali earth metal carbonate, talc, mica, zeolite and combinations thereof.
71. The composition of any one of paragraphs 66 to 70, wherein the inorganic particulate mineral is calcium carbonate, for example precipitated calcium carbonate (PCC).
72. The composition of any one of paragraphs 66 to 71, wherein the inorganic particulate mineral is not coral sand and/or is not derived from coral sand.
73. The composition of any one of paragraphs 66 to 72, wherein the inorganic particulate mineral is synthetic, for example is synthetic calcium carbonate (e.g. PCC), synthetic talc, synthetic mica, synthetic zeolite or combinations thereof.
74. The composition of any one of paragraphs 66 to 73, wherein at least about 90% of particles of the inorganic particulate mineral and/or particles of antimicrobial metal compound are smaller than 5 microns.
75. The composition of any one of paragraphs 66 to 74, wherein at least about 50% of particles of the inorganic particulate mineral and/or particles of antimicrobial metal compound are smaller than 2 microns.
76. The composition of any one of paragraphs 66 to 75, wherein the composition is an aqueous slurry.
77. The composition of paragraph 76, wherein the aqueous slurry has a solids content of at least about 50 wt %, for example at least about 60 wt %.
78. The composition of paragraph 76 or 77, wherein the aqueous slurry has a Brookfield viscosity equal to or less than about 1200 mPa·s.
79. The composition of any one of paragraphs 66 to 78, wherein the antimicrobial metal is selected from the group consisting of silver, cobalt, nickel, copper, iron, mercury, lead, zinc, zirconium, molybdenum, bismuth, gold, aluminium, magnesium, niobium, silicon, tantalum, hafnium, lanthanum, tungsten, calcium, titanium, vanadium, cerium, strontium, tin, lithium and combinations thereof, for example wherein the antimicrobial metal is silver.
80. The composition of any one of paragraphs 66 to 79, wherein the antimicrobial metal is present in the composition in an amount ranging from about 0.1% to about 10%, for example from about 0.2% to about 5%, by weight of the inorganic particulate mineral.
81. The composition of any one of paragraphs 66 to 80, wherein the antimicrobial metal compound is a compound that may be made as a by-product of a process to make the inorganic particulate mineral.
82. The composition of any one of paragraphs 66 to 81, wherein the inorganic particulate mineral is or comprises an alkali earth metal carbonate and the antimicrobial metal compound is antimicrobial metal carbonate.
83. The composition of any one of paragraphs 66 to 81, wherein the inorganic particulate mineral is or comprises one or more of talc, mica and zeolite and the antimicrobial metal compound is antimicrobial metal silicate.
84. The composition of any one of paragraphs 66 to 83, wherein the antimicrobial metal compound particles are physically bonded to the inorganic particulate mineral particles to form an aggregate.
85. The composition of paragraph 84, wherein the antimicrobial metal compound particles are physically bonded to the inorganic particulate mineral particles by one or more of Van der Waals forces, London dispersion forces, dipole-dipole interactions, hydrogen bonding and Debye force (induced dipole).
86. The composition of paragraph 84 or 85, wherein the antimicrobial metal compound particles are distributed, for example evenly distributed, throughout the aggregate.
87. The composition of paragraph 84 or 86, wherein the antimicrobial metal compound particles are positioned at the core of the aggregate.
88. The composition of any one of paragraphs 66 to 87, wherein the composition has a toxic effect on one or more microbes.
89. The composition of any one of paragraphs 66 to 88, wherein the composition is substantially devoid, for example devoid, of biocide.
90. The composition of any one of paragraphs 66 to 89, wherein the composition is substantially devoid, for example devoid, of microbes.
91. A method of making a composition of any one of paragraphs 1 to 65, comprising combining the inorganic particulate mineral and the antimicrobial metal.
92. The method of paragraph 91, wherein the inorganic particulate mineral is a synthetic inorganic particulate mineral and the antimicrobial metal is combined with the inorganic particulate mineral during preparation of the synthetic inorganic particulate mineral.
93. The method of paragraph 91 or 92, wherein the antimicrobial metal is in the form of a metal salt.
94. The method of any one of paragraphs 91 to 93, wherein the antimicrobial metal is in the form of a metal halide, for example a metal chloride, or a metal nitrate.
95. A method of making a composition of any one of paragraphs 48 to 65, comprising preparing precipitated calcium carbonate (PCC) in the presence of the antimicrobial metal.
96. The method of paragraph 95, wherein the antimicrobial metal is a metal salt.
97. The method of paragraph 95 or 96, wherein the antimicrobial metal is a metal halide, for example a metal chloride, or a metal nitrate.
98. A method of making a composition of any one of paragraphs 66 to 90, comprising combining the inorganic particulate mineral and the antimicrobial metal compound.
99. The method of paragraph 98, wherein the inorganic particulate mineral is a synthetic inorganic particulate mineral and the antimicrobial metal compound is formed during preparation of the synthetic inorganic particulate mineral.
100. The method of any one of paragraphs 97 or 99, wherein the antimicrobial metal compound is a compound that would result from the reaction of the inorganic particulate mineral with the antimicrobial metal or is a by-product of a process for forming the inorganic particulate mineral.

101. The method of any one of paragraphs 97 to 100, wherein the inorganic particulate mineral is or comprises an alkali earth metal carbonate and the antimicrobial metal compound is antimicrobial metal carbonate.

102. The method of any one of paragraphs 97 to 100, wherein the inorganic particulate mineral is or comprises one or more of talc, mica and zeolite and the antimicrobial metal compound is antimicrobial metal silicate.

103. Use of a composition of any one of the preceding paragraphs to inhibit the growth of one or more microbes or to reduce the number or substantially eliminate, for example eliminate, one or more microbes.

104. A coating composition comprising a polymeric binder and a composition of any one of the preceding paragraphs.

105. Use of a composition of any one of the preceding paragraphs in a coating composition comprising a polymeric binder.

106. The use of paragraph 105, wherein the coating composition inhibits the growth of one or more microbes on the substrate on which the coating composition is/is intended to be applied and/or in the coating composition and/or on the coating composition.

107. Use of a composition of any one of the preceding paragraphs to substantially remove, for example remove, one or more microbes from a liquid.

108. The use of paragraph 107, wherein the liquid is water.

109. The use of paragraph 108, wherein one or more microbes is removed from the water to make it suitable for animal, for example human, consumption.

110. Use of a composition of any one of the preceding paragraphs as a polymer additive.

111. A polymeric article comprising a polymer and a composition of any one of the preceding paragraphs.

EXAMPLES

Precipitated calcium carbonate was made using slaked lime in a laboratory scale reactor with citric acid at 55° C. by adding carbon dioxide gas. Silver chloride or silver nitrate was added after 20 minutes of carbonation to form precipitated calcium carbonate comprising 0.3 wt %, 0.6 wt % and 3 wt % silver. In order to provide 0.3 wt % silver (molecular weight 107.87) in the finished PCC, 4.72 g of silver nitrate (molecular weight 169.87) per kg of finished PCC is required (0.47%).

After over-carbonation, the XRF Protrace and total silver of the composition was measured by wet chemical analysis using the nitric acid test method. The screened PCC may undergo the normal tests, for example for brightness, surface area, SEM.

This antimicrobial PCC material was tested for antimicrobial activity by taking known highly contaminated carbonate slurry and adding amounts of the antimicrobial PCC (from 50 to 5000 ppm), on its own or in combination with other biocidal substances such as hydrogen peroxide. Bacteria levels were measured as described above using conventional dipslides/petrifilm after incubation for 48 hours, 1 week, 2 weeks, 3 weeks and 4 weeks. In addition, the antimicrobial PCC material was added to a known uncontaminated carbonate slurry and the carbonate slurry was inoculated with typical bacteria strains associated with the calcium carbonate slurry (e.g. *Pseudomonas taetrolens,* *Pseudomonas stutzeri, Marinilabilia salmonicator, Caldimonas manganoxidans, Pseudomonas fluorens, Pseudomonas putida, Bacillus cereus, Pseudomonas aeruginosa, Alkaliphilus transvaalenis, Alicyclobacillus acidocadarum, Pseudomonas tolaasii, Clostridium argentiense, Edwardsiella tarda, Clostridium thermopalmarium, Polynuclobacter necessaries, Comamonas aquatica, Tissierella creatinine, Azotobacter chroococcum, Pseudomonas mossellii, Methylobacterium brachiatum*). It was found that the antimicrobial PCC materials possessed antimicrobial activity.

The invention claimed is:

1. A composition comprising
   particles of an inorganic particulate mineral and
   particles of an antimicrobial metal,
   wherein the particles of antimicrobial metal are greater than 50 nm in size and are incorporated within the particles of the inorganic particulate mineral,
   wherein the particles of inorganic particulate mineral do not include silver nanoparticles embedded in their structure,
   wherein the particles of inorganic particulate mineral do not comprise pores,
   wherein the inorganic particulate mineral is selected from the group consisting of alkali earth metal carbonate, talc, mica, zeolite and combinations thereof, and
   wherein the antimicrobial metal is selected from the group consisting of silver, cobalt, nickel, copper, iron, mercury, lead, zinc, zirconium, molybdenum, bismuth, gold, aluminium, magnesium, niobium, silicon, tantalum, hafnium, lanthanum, tungsten, titanium, vanadium, cerium, strontium, tin, lithium and combinations thereof.

2. The composition of claim 1, wherein the inorganic particulate mineral has a steepness factor of at least about 10.

3. The composition of claim 1, wherein the inorganic particulate mineral is calcium carbonate.

4. The composition of claim 1, wherein the inorganic particulate mineral is calcite.

5. The composition of claim 1, wherein the inorganic particulate mineral comprise synthetic calcium carbonate, synthetic talc, synthetic mica, synthetic zeolite, or combinations thereof.

6. The composition of claim 1, wherein at least about 90% of particles of the inorganic particulate mineral are smaller than 5 microns.

7. The composition of claim 1, wherein at least about 50% of particles of the inorganic particulate mineral are smaller than 2 microns.

8. The composition of claim 1, wherein the composition is an aqueous slurry.

9. The composition of claim 8, wherein the aqueous slurry has a solids content of at least about 50 wt%.

10. The composition of claim 8, wherein the aqueous slurry has a Brookfield viscosity equal to or less than about 1200 mPa.s.

11. The composition of claim 1, wherein the particles of antimicrobial metal are present in the composition in an amount ranging from about 0.1% to about 10%, by weight of the inorganic particulate mineral.

12. The composition of claim 1, wherein the particles of antimicrobial metal are chemically bonded to the inorganic particulate mineral.

13. The composition of claim 1, wherein the particles of antimicrobial metal are physically bonded to the inorganic particulate mineral.

14. The composition of claim 1, wherein the particles of antimicrobial metal are distributed throughout the particles of the inorganic particulate mineral.

15. The composition of claim 1, wherein the particles of antimicrobial metal are positioned at the core of the particles of the inorganic particulate mineral.

16. The composition of claim 1, wherein the inorganic particulate mineral comprises precipitated calcium carbonate (PCC).

17. The composition of claim 1, wherein the antimicrobial metal is silver.

* * * * *